United States Patent [19]

Axen

[11] 4,205,178
[45] May 27, 1980

[54] 6-KETO PROSTAGLANDIN E-TYPE COMPOUNDS

[75] Inventor: Udo F. Axen, Plainwell, Mich.

[73] Assignee: The Upjohn Company, Kalamazoo, Mich.

[21] Appl. No.: 829,679

[22] Filed: Sep. 2, 1977

Related U.S. Application Data

[63] Continuation-in-part of Ser. No. 755,675, Dec. 30, 1976, abandoned.

[51] Int. Cl.$^2$ ........................................... C07C 177/00
[52] U.S. Cl. ..................... 560/121; 260/404; 260/404.5; 260/408; 260/410; 260/410.9 R; 260/410.5; 260/413; 560/231; 562/503
[58] Field of Search ............... 260/514 D, 404, 404.5, 260/408, 410, 410.5, 410.9 R, 413; 560/121, 231; 562/503

[56] References Cited

FOREIGN PATENT DOCUMENTS 2509415  9/1975  Fed. Rep. of Germany ........... 260/514

OTHER PUBLICATIONS

Tanaka et al., Tet. Letters, 1535 (1975).

*Primary Examiner*—Robert Gerstl
*Attorney, Agent, or Firm*—Robert A. Armitage; Morris L. Nielsen

[57] ABSTRACT

Prostaglandin E (PGE)-type derivatives and analogs having a 6-keto feature are disclosed, including processes for preparing them and the appropriate intermediates, said derivatives having pharmacological activity.

A typical 6-keto compound is 6-keto-PGE$_1$, methyl ester, represented by the formula:

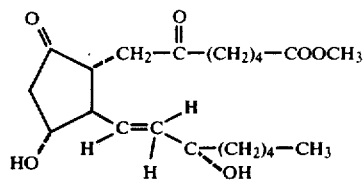

44 Claims, No Drawings

6-KETO PROSTAGLANDIN E-TYPE COMPOUNDS

CROSS REFERENCE TO RELATED APPLICATIONS

This application is a continuation-in-part of copending application Ser. No. 755,675 filed Dec. 30, 1976, now abandoned.

BACKGROUND OF THE INVENTION

This invention relates to prostaglandin derivatives and to a process for preparing them.

The prostaglandins and analogs are well-known organic compounds derived from prostanoic acid which has the following structure and atom numbering:

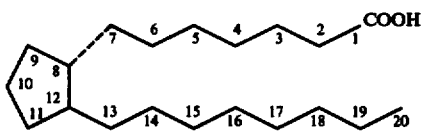

As drawn hereinafter the formulas represent a particular optically active isomer having the same absolute configuration as $PGE_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

SUMMARY OF THE INVENTION

It is the purpose of this invention to provide novel products having pharmacological activity. It is a further purpose to provide a process for preparing these products and their intermediates.

Accordingly, there is provided an optically active compound of the formula

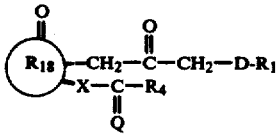

I or a mixture comprising that compound and the enantiomer thereof, including the lower alkanoates.

In formula I and in other formulas hereinafter including formulas in the Charts, the terms D, L, Q, $R_1$, and the like are as defined in the TABLE. Reference to that Table will establish what is intended to be represented by each formula.

In formula I as used herein, attachment to ⓡ$_{18}$ corresponds to bonds to the cyclopentane ring at the C-8, C-9, and C-12 positions following prostaglandin nomenclature, thus

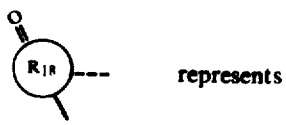

and, similarly, in formulas III and IV

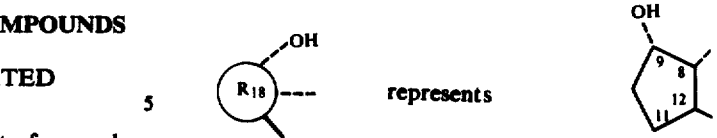

Within the scope of the prostaglandin derivatives described herein there are represented (a) PGE compounds when 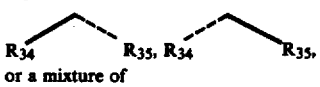 is

TABLE

DEFINITION OF TERMS FOR FORMULAS

D is
(1) $-(CH_2)_d-C(R_2)_2-$
(2) $-CH_2-O-CH_2-Y-$ or
(3) $-CH_2CH=CH-$
wherein d is zero to 5, $R_2$ is hydrogen, methyl, or fluoro, being the same or different with the proviso that one $R_2$ is not methyl when the other is fluoro, and Y is a valence bond, $-CH_2-$, or $-(CH_2)_2-$.

$D_1$ is
the same as D above but without $-CH_2CH=CH-$.

$L_1$ is

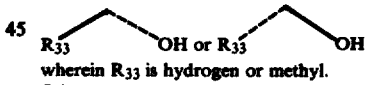

or a mixture of

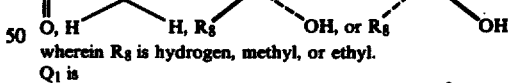

wherein $R_{34}$ and $R_{35}$ are hydrogen, methyl, or fluoro, being the same or different, with the proviso that one of $R_{34}$ and $R_{35}$ is fluoro only when the other is hydrogen or fluoro;

$L_2$ and $L_3$ are
hydrogen, alkyl of one to 4 carbon atoms, inclusive, or $-COOR_{32}$, wherein $R_{32}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive; being the same or different, with the proviso that not more than one of $L_2$ and $L_3$ is $-COOR_{32}$.

$M_1$ is

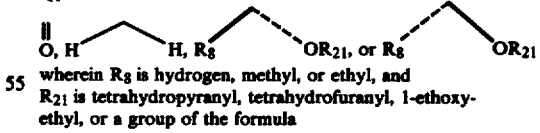

wherein $R_{33}$ is hydrogen or methyl.

Q is

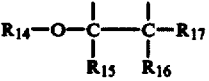

wherein $R_8$ is hydrogen, methyl, or ethyl.

$Q_1$ is $\underset{O,}{\overset{\|}{}} H \quad \diagdown\diagup H, R_8 \quad \diagdown\diagup OR_{21}, \text{ or } R_8 \diagdown\diagup OR_{21}$ wherein $R_8$ is hydrogen, methyl, or ethyl, and $R_{21}$ is tetrahydropyranyl, tetrahydrofuranyl, 1-ethoxyethyl, or a group of the formula $$R_{14}-O-\underset{\underset{R_{15}}{|}}{\overset{\overset{H}{|}}{C}}-\underset{\underset{R_{16}}{|}}{\overset{|}{C}}-R_{17}$$

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, $-(CH_2)_a-$ or $-(CH_2)_b-O-(CH_2)_c-$ wherein a is 3, 4, or 5,

4,205,178

TABLE-continued
DEFINITION OF TERMS FOR FORMULAS b is one, 2, or 3, and c is one, 2, or 3 with the
proviso that b plus c is 2, 3, or 4, and wherein $R_{17}$
is hydrogen or phenyl.

$Q_2$ is

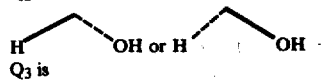

$Q_3$ is

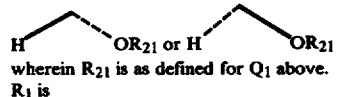

wherein $R_{21}$ is as defined for $Q_1$ above.

$R_1$ is (1) —COOR$_3$ (2) —CH$_2$OH (3) —CH$_2$N(R$_9$)(R$_{28}$)

(4) —C(=O)—N(R$_9$)(R$_{28}$) or (5) —C(=NH—N, N=N)

wherein $R_3$ is (a) hydrogen, (b) alkyl of one to 12
carbon atoms, inclusive, (c) cycloalkyl of 3 to 10
carbon atoms, inclusive, (d) aralkyl of 7 to 12 carbon atoms, inclusive, (e) phenyl, (f) phenyl substituted with one, 2, or 3 chloro or alkyl of one to
4 carbon atoms, inclusive, (g) 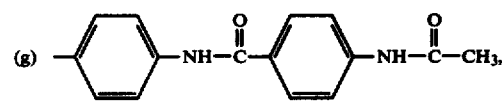

(h) 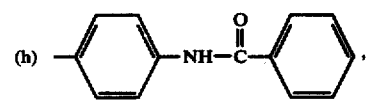

(i) 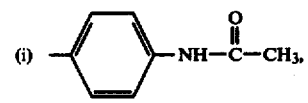

(j) 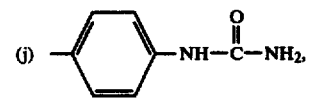

(k) 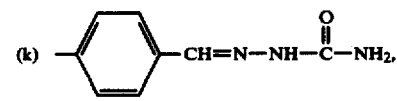

(l) 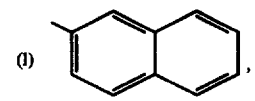

(m) 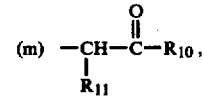

wherein $R_{10}$ is phenyl, p-bromophenyl, p-biphenylyl,
p-nitrophenyl, p-benzamidophenyl, or 2-naphthyl,
and wherein $R_{11}$ is hydrogen or benzoyl, or (n) a pharmacologically acceptable cation,
wherein $R_9$ is hydrogen, methyl, or ethyl, and $R_{28}$ is
hydrogen, alkyl of one to 4 carbon atoms, inclusive,
aralkyl of 7 to 12 carbon atoms, inclusive, phenyl,
on phenyl substituted with alkyl of one to 4 carbon
atoms, inclusive.

$R_2$ is
hydrogen, methyl, or fluoro, being the same or different with the proviso that one $R_2$ is not methyl
when the other is fluoro.

$R_3$ is
(a) hydrogen, (b) alkyl of one to 12 carbon atoms,
inclusive, (c) cycloalkyl of 3 to 10 carbon atoms,
inclusive, (d) aralkyl of 7 to 12 carbon atoms,

TABLE-continued
DEFINITION OF TERMS FOR FORMULAS inclusive, (e) phenyl, (f) phenyl substituted with
one, 2, or 3 chloro or alkyl of one to 4 carbon atoms,
inclusive, (g) 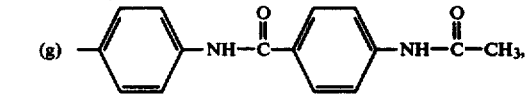

(h) 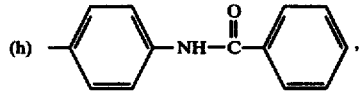

(i) 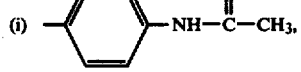

(j) 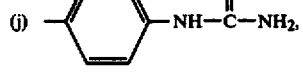

(k) 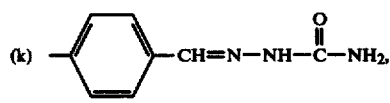

(l) 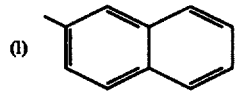

(m) 

wherein $R_{10}$ is phenyl, p-bromophenyl, p-biphenylyl,
p-nitrophenyl, p-benzamidophenyl, or 2-naphthyl,
and wherein $R_{11}$ is hydrogen or benzoyl, or (n) a pharmacologically acceptable cation.

$R_4$ is (1) 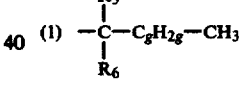

(2) 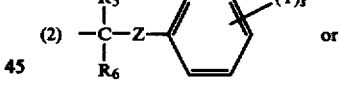 or (3) 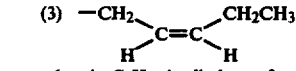

wherein $C_gH_{2g}$ is alkylene of one to 9 carbon atoms,
inclusive, with one to 5 carbon atoms, inclusive, in
the chain between —CR$_5$R$_6$— and terminal methyl, wherein
$R_5$ and $R_6$ are hydrogen, alkyl of one to 4 carbon atoms,
inclusive, or fluoro, being the same or different, with
the proviso that one of $R_5$ and $R_6$ is fluoro only when
the other is hydrogen or fluoro and the further proviso
that neither $R_5$ nor $R_6$ is fluoro when Z is oxa (—O—);
wherein Z represents an oxa atom (—O—) or $C_jH_{2j}$ wherein $C_jH_{2j}$ is a valence bond or alkylene of one to 9
carbon atoms, inclusive, with one to 6 carbon atoms,
inclusive, in the chain between CR$_5$R$_6$— and the phenyl
ring;
wherein T is alkyl of one to 4 carbon atoms, inclusive,
fluoro, chloro, trifluoromethyl, or alkoxy of one to
4 carbon atoms, inclusive, and s is zero, one, 2 or 3,
with the proviso that not more than two T's are other
than alkyl and when s is 2 or 3 the T's are either the
same or different.

$R_5$ and $R_6$ are
hydrogen, alkyl of one to 4 carbon atoms, inclusive,
or fluoro, being the same or different, with the
proviso that one of $R_5$ and $R_6$ is fluoro only when
the other is hydrogen or fluoro and the further proviso
that neither $R_5$ nor $R_6$ is fluoro when Z is oxa (—O—).

TABLE-continued
DEFINITION OF TERMS FOR FORMULAS $R_7$ is

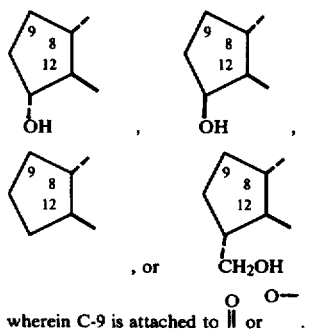

wherein C-9 is attached to ∥ or .

$R_8$ is
hydrogen, methyl, or ethyl.
$R_9$ is
hydrogen, methyl, or ethyl.
$R_{10}$ is
phenyl, p-bromophenyl, p-phenylyl, p-nitrophenyl, p-benzamidophenyl, or 2-naphthyl.
$R_{11}$ is
hydrogen or benzoyl.
$R_{14}$ is
alkyl of one to 18 carbon atoms, inclusive, cycloalkyl of 3 to 10 carbon atoms, inclusive, aralkyl of 7 to 12 carbon atoms, inclusive, phenyl or phenyl substituted with one, 2, or 3 alkyl of one to 4 carbon atoms, inclusive.
$R_{15}$ and $R_{16}$ are
the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{15}$ are taken together, $-(CH_2)_a-$ or $-(CH_2)_b-O-(CH_2)_c-$ wherein a is 3, 4, or 5, b is one, 2, or 3, and c is one, 2, or 3 with the proviso that b plus c is 2, 3, or 4.
$R_{17}$ is
hydrogen or phenyl.

$R_{18}$ is

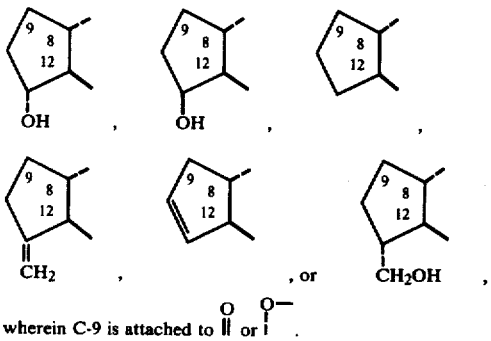

wherein C-9 is attached to ∥ or .

$R_{19}$ is
(1) $-COOR_{20}$
(2) $-CH_2OH$
(3) $-CH_2N(R_9)(R_{28})$
(4) $-C-N(R_9)(R_{28})$ or
(5) $-C\begin{smallmatrix}NH-N\\ \|\\ N\rule{1em}{0.5pt}N\end{smallmatrix}$ wherein $R_{20}$ is the same as $R_3$ above except that it does not include "(n) a pharmacologically acceptable cation", and $R_9$ and $R_{28}$ are as defined herein.
$R_{20}$ is
the same as $R_3$ above except that it does not include "(n) a pharmacologically acceptable cation".

TABLE-continued
DEFINITION OF TERMS FOR FORMULAS $R_{21}$ is
tetrahydropyranyl, tetrahydrofuranyl, 1-ethoxyethyl, or a group of the formula $R_{14}-O-\underset{R_{15}}{\overset{H}{\underset{|}{C}}}-\underset{R_{16}}{\overset{|}{C}}-R_{17}$ wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, $-(CH_2)_a-$ or $-(CH_2)_b-O-(CH_2)_c-$ wherein a is 3, 4, or 5, b is one, 2, or 3, and c is one, 2, or 3 with the proviso that b plus c is 2, 3, or 4, and wherein $R_{17}$ is hydrogen or phenyl.

$R_{22}$ is

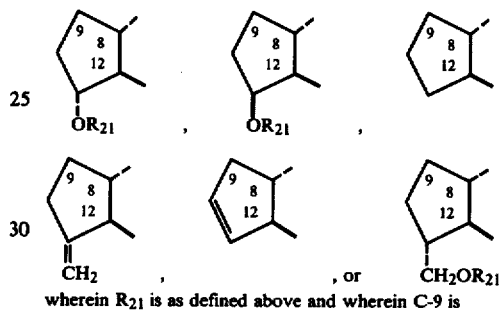

wherein $R_{21}$ is as defined above and wherein C-9 is attached to ∥ or .

$R_{23}$ is
(1) $-COOR_{20}$
(2) $-CH_2OR_{21}$
(3) $-CH_2N(R_9)(R_{28})$
(4) $-\overset{O}{\underset{\|}{C}}-N(R_9)(R_{28})$ or
(5) $-C\begin{smallmatrix}NH-N\\ \|\\ N\rule{1em}{0.5pt}N\end{smallmatrix}$ wherein $R_9$, $R_{20}$, $R_{21}$ and $R_{28}$ are as defined herein.
$R_{26}$ is (1) $-\underset{R_6}{\overset{R_5}{\underset{|}{\overset{|}{C}}}}-C_gH_{2g}-CH_3$ or (2) $-\underset{R_6}{\overset{R_5}{\underset{|}{\overset{|}{C}}}}-Z-\underset{}{\underset{}{\overset{}{\bigcirc}}}^{(T)_s}$ wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa $(-O-)$; wherein Z represents an oxa atom $(-O-)$ or $C_jH_{2j}$ wherein $C_jH_{2j}$ is a valence bond or alkylene of one to 9 carbon atoms, inclusive, with one to 6 carbon atoms, inclusive between $CR_5R_6-$ and the phenyl ring; wherein T is alkyl of one to 4 carbon atoms, inclusive, fluoro, chloro, trifluoromethyl, of alkoxy of one to 4 carbon atoms, inclusive, and s is zero, one, 2 or 3, with the proviso that not more than two T's are other than alkyl and when s is 2 or 3 the T's are either the same or different.

TABLE-continued
DEFINITION OF TERMS FOR FORMULAS $R_{28}$ is
hydrogen, alkyl of one to 4 carbon atoms, inclusive,
aralkyl of 7 to 12 carbon atoms, inclusive, phenyl,
or phenyl substituted with alkyl of one to 4 carbon
atoms, inclusive.

$R_{29}$ is
bromo or chloro.

$R_{30}$ is
(1) $-(CH_2)_m-CH_3$, (2) 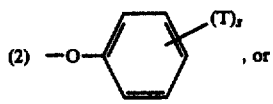, or (3) 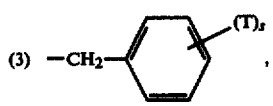, wherein m is one to 5, inclusive, T is chloro, fluoro,
trifluoromethyl, alkyl of one to 4 carbon atoms, inclusive, or alkoxy of one to 4 carbon atoms, inclusive,
and s is zero, one, 2, or 3, the various T's being the
same or different, with the proviso that not more than
two T's are other than alkyl, with the further proviso
that $R_{30}$ is

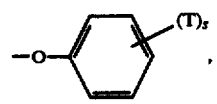, wherein T and s are as defined above, only when $R_{34}$
and $R_{35}$ as defined above for $L_1$ are hydrogen or methyl,
being the same or different.

$R_{31}$ is
hydrogen or hydroxy.

$R_{32}$ is
hydrogen, alkyl of one to 12 carbon atoms, inclusive,
cycloalkyl of 3 to 10 carbon atoms, inclusive, aralkyl
of 7 to 12 carbon atoms, inclusive, phenyl, or phenyl
substituted with one, 2, or 3 chloro or alkyl of one
to 4 carbon atoms, inclusive.

$R_{33}$ is
hydrogen or methyl.

$R_{34}$ and $R_{35}$ are
hydrogen, methyl, or fluoro, being the same or different, with the proviso that one of $R_{34}$ and $R_{35}$ is
fluoro only when the other is hydrogen or fluoro.

$(R_{36})$ is

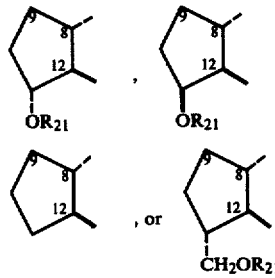

wherein $R_{21}$ is as defined above and wherein C-9 is
attached to $\overset{O}{\underset{\|}{}}$ or $\overset{O-}{\underset{|}{}}$.

$R_{37}$ is
iodo, bromo, or chloro.

T is
alkyl of one to 4 carbon atoms, inclusive, fluoro,
chloro, trifluoromethyl, or alkoxy of one to 4 carbon
atoms, inclusive, with the proviso that not more than
two T's are other than alkyl and when s is 2 or 3 the
T's are either the same or different.

$V_1$ is
(1) cis-$CH=CH-CH_2-(CH_2)_p-CH_2-$,
(2) cis-$CH=CH-CH_2-(CH_2)_p-CF_2-$,
(3) cis-$CH=CH-D-$
wherein D is as defined above and p is one, 2, or 3.

TABLE-continued
DEFINITION OF TERMS FOR FORMULAS

X is
(1) trans-$CH=CH-$
(2) cis-$CH=CH-$
(3) $-C\equiv C-$ or
(4) $-CH_2CH_2-$.

$X_1$ is
(1) trans-$CH=CH-$
(2) $-C\equiv C-$ or
(3) $-CH_2CH_2-$.

Y is
a valence bond, $-CH_2-$ or $-(CH_2)_2-$.

Z is
an oxa atom ($-O-$) or $C_jH_{2j}$ wherein $C_jH_{2j}$ is a valence
bond or alkylene of one to 9 carbon atoms, inclusive,
with one to 6 carbon atoms, inclusive in the chain
between $-CR_5R_6-$ and the phenyl ring.

a is
3, 4, or 5.

b is
one, 2, or 3.

c is
one, 2, or 3.

d is
zero to 5, inclusive.

f is
zero to 4.

m is
one to 5, inclusive.

p is
one, 2, or 3.

s is
zero, one, 2, or 3.

$C_gH_{2g}$ is
alkylene of one to 9 carbon atoms, inclusive, with one
to 5 carbon atoms, inclusive, in the chain between
$-CR_5R_6-$ and terminal methyl.

$C_jH_{2j}$ is
a valence bond or alkylene of one to 9 carbon atoms,
inclusive, with one to 6 carbon atoms, inclusive, in
the chain between $-CR_5R_6-$ and the phenyl ring.

In formula I as used herein, attachment to 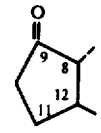
corresponds to bonds to the cyclopentane ring at the
C-8, C-9, and C-12 positions following prostaglandin
nomenclature, thus

 represents and, similarly, in formulas III and IV

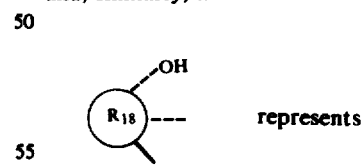 represents 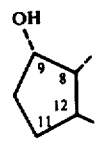

Within the scope of the prostaglandin derivatives described herein there are represented (a) PGE compounds when 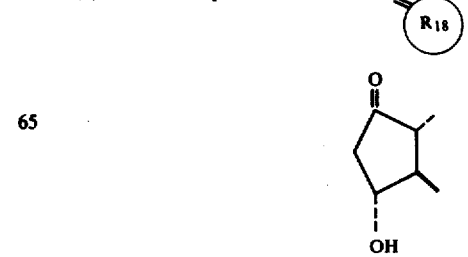 is (b) 11β-PGE compounds when

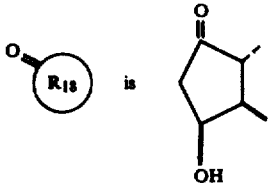

(c) 11-Deoxy-PGE compounds when

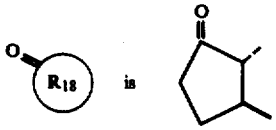

(d) 11-Deoxy-11-methylene-PGE compounds when

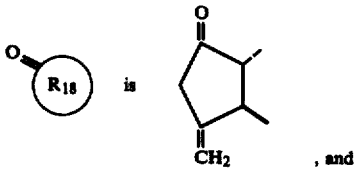

, and (e) 11-Deoxy-11-hydroxymethyl-PGE compounds when

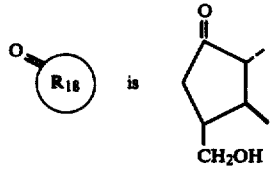

Further within the scope of the prostaglandin derivatives described herein there are represented (a) PGE-type acids, esters and salts when $R_1$ is —COOR$_3$, (b) 2-Decarboxy-2-hydroxymethyl-PGE type compounds when $R_1$ is —CH$_2$OH, (c) 2-Decarboxy-2-amino-PGE type compounds when $R_1$ is —CH$_2$N(R$_9$)(R$_{28}$), (d) PGE-type amides when $R_1$ is

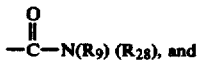

and (e) 2-Decarboxy-2-tetrazol-1-yl-PGE type compounds when $R_1$ is

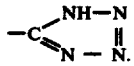

For those compounds of formula I wherein Q is

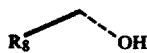

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula I when Q is

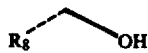

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

A typical example of the compounds of formula I is represented by the formula

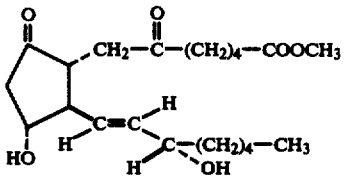

and named 6-keto-PGE$_1$, methyl ester. The formula-II compound is a species of the formula-I compounds wherein D is —(CH$_2$)$_3$—, Q is

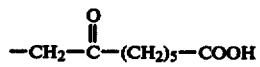

$R_1$ is COOCH$_3$, $R_4$ is n-pentyl,

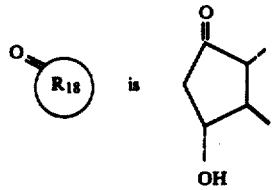

and X is trans—CH=CH—.

Regardless of the number of carbon atoms in the chain between the keto group and the terminal $R_1$ group, these compounds are regarded as "6-keto" compounds, from the designation of C-6 in the basic PGE$_1$ formula referring back to the prostanoic acid skeleton. Compounds having longer or shorter chains are named following the accepted conventions using "homo" or "nor". For example the side chain $$-CH_2-\overset{O}{\overset{\|}{C}}-(CH_2)_5-COOH$$

is named "2a-homo-6-keto . . . ", whereas $$-CH_2-\overset{O}{\overset{\|}{C}}-(CH_2)_3-COOH$$

is named "2-nor-6-keto . . . ".

The products of this invention within the scope of formula I are extremely potent in causing various biological responses. For that reason, these compounds are useful for pharmacological purposes. A few of those biological responses are: inhibition of blood platelet aggregation, stimulation of smooth muscle, systemic blood pressure lowering, inhibiting gastric secretion and reducing undesirable gastrointestinal effects from systemic administration of prostaglandin synthetase inhibitors, controlling spasm and facilitating breathing in asthmatic conditions, decongesting nasal passages, affecting the reproductive organs of mammals as labor inducers, abortifacients, cervical dilators, regulators of the estrus, and regulators of the menstrual cycle, accelerating growth of epidermal cells and keratin in animals, and alleviating the symptoms of proliferating skin diseases.

Because of these biological responses, these novel compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

These compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of these compounds to whole blood provides in vitro applications such as, storage of whole blood to be used in heart-lung machines. Additionally whole blood containing these compounds can be circulated through organs, e.g. heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 $\mu$g/ml of whole blood.

These compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

These compounds are useful as hypotensive agents to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

These prostaglandin derivatives are useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. to about 20 $\mu$g. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors. The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin derivative is administered along with the anti-inflammatory prostaglandin synthetase inhibitor either by the same route of administration or by a different route. For example, if the anti-inflammatory substance is being administered orally, the prostaglandin derivative is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin derivative is also administered rectally. Further, the prostaglandin derivative can be conveniently administered orally or, in the case of women, vaginally. It is especially convenient when the administration route is to be the same for both anti-inflammatory substance and prostaglandin derivative, to combine both into a single dosage form.

The dosage regimen for the prostaglandin derivative in accord with this treatment will depend upon a variety of factors, including the type, age, weight, sex and medical condition of the mammal, the nature and dosage regimen of the anti-inflammatory, synthetase inhibitor being administered to the mammal, the sensitivity of the particular prostaglandin derivative to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin derivative to reduce and then substantially to eliminate those undesirable effects.

These compounds are also useful in the treatment of asthma. For example, these compound are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation.

For administration by the oral inhalation route with conventional nebulizers or by oxygen aerosolization it is convenient to provide the instant active ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, sodium bissulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

These compounds are useful in mammals, including man, as nasal decongestants and are used for this purpose in a dose range of about 10 µg. to about 10 mg. per ml. of a pharmacologically suitable liquid vehicle or as an aerosol spray, both for topical application.

These compounds are also usful in treating peripheral vascular disease in humans. The term peripheral vascular disease as used herein means disease of any of the blood vessels outside of the heart and to disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease. For these conditions the compounds of this invention are administered orally or parenterally via injection or infusion directly into a vein or artery, intra-venous or intra-arterial injections being preferred. The dosages of these compounds are in the range of 0.01-1.0 µg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

These compounds are accordingly useful for treating peripheral vascular diseases in the extremities of humans who have circulatory insufficiencies in said extremities, such treatment affording relief of rest pain and induction of healing of ulcers. For complete discussion of the nature of and clinical manifestations of human peripheral vascular disease and the method previously known of its treatment with prostaglandins see South African Pat. No. 74/0149 referenced as Derwent Farmdoc No. 58,400V. See Elliott, et al., Lancet, Jan. 18, 1975, pp. 140–142.

These compounds which are useful in place of oxytocin to induce labor are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 µg. per kg. of body weight per minute until or near the termination of the second stage of labor, i.e. expulsion of the fetus. These compounds are especially useful when the female is one or more weeks post-mature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating the female mammals is meant animals which are mature enough to menstruate, but not so old that regular menstruation has ceased. For that purpose the prostaglandin derivative is administered systemically at a dose level in the range 0.01 mg. to about 20 mg. per kg. of body weight of the female mammal, advantageously during a span of time starting approximately at the time of ovulation and ending approximately at the time of mensus or just prior to mensus. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin derivative is administered locally or systemically.

The prostaglandin derivative, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births then the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin derivative 5 to 8 days after ovulation and return to estrus. Cattle are treated at regular intervals over a 3 week period to advantageously bring all into estrus at the same time.

These compounds including the salts increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, including humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the cite where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 µg. per ml. of the prostaglandin derivative. Especially for topical use, these compounds are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

These prostaglandin derivatives are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

These compounds are applied topically as compositions including a suitable pharmaceutical carrier, for example, as an ointment, lotion, paste, jelly, spray, or aerosol, using typical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or peri-lesionally, or subcutaneously, using appropriate sterile saline compositions.

These compounds are useful as anti-inflammatory agents for inhibiting chronic inflammation in mammals including the swelling and other unpleasant effects thereof using methods of treatment and dosages generally in accord with U.S. Pat. No. 3,885,041, which patent is incorporated herein by reference.

Many of the biological responses known for these 6-keto prostaglandin derivatives are also known for the older prostaglandin compounds. However, these derivatives are surprisingly more specific with regard to potency in causing prostaglandin-like biological responses. Each of these novel derivatives is therefore useful in place of the known prostaglandin-type compounds for at least one of the above pharmacological purposes and, moreover, is surprisingly and unexpectedly more useful for that purpose because it causes smaller and fewer undesired side effects than the known prostaglandins.

Furthermore, these novel compounds are administered effectively orally, sublingually, intravaginally, buccally, or rectally, in addition to usual intravenous, intramuscular, or subcutaneous injection or infusion methods used for the known prostaglandins. These qualities are advantageous because they facilitate maintaining uniform levels of these compounds in the body with fewer, shorter, or smaller doses, and make possible self-administration by the patient.

There are further provided the various processes for preparing the 6-keto compounds of formula-I. Thus, one process comprises the steps of starting with a compound of the formula

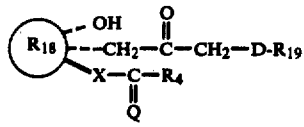

and (a) transforming that starting compound to a compound of the formula

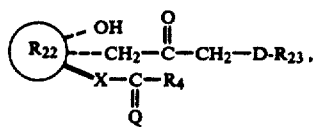

(b) subjecting the product of step (a) to oxidation to form a compound of the formula

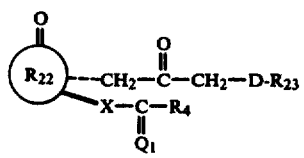

and (c) transforming the product of step (b) to a compound of the formula

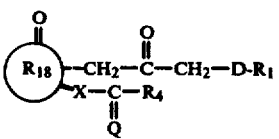

Reference to Chart A herein will make clear the steps of that process.

The starting materials of formula III are not the subject of this invention but will be described at a later point in this application. The 6-keto compounds of formula III are in equilibrium with and therefore accompanied by hemi-ketal compounds of the formula

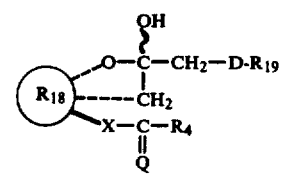

CHART A

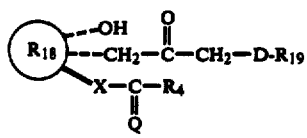

↓ (a)

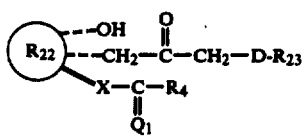

↓ (b)

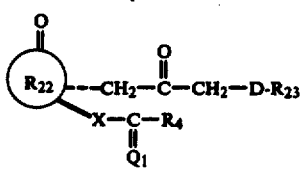

↓ (c)

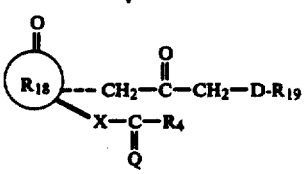

In step "a" of Chart A the starting material III is transformed to a corresponding formula-IV compound.

When the blocking group $R_{21}$ is $Q_1$, $R_{22}$ and $R_{23}$ in tetrahydropyranyl or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess, preferably 1.0 to 1.2 times theory, and the reaction is carried out at about 20°–50° C.

When $R_{21}$ is of the formula

as defined herein, including 1-ethoxyethyl, the appropriate reagent is a vinyl ether, e.g. ethyl vinyl ether, isoproenyl methyl ether, isobutyl vinyl ether, or any vinyl ether of the formula $R_{14}-O-C(R_{15})=CR_{16}R_{17}$ wherein $R_{14}$, $R_{15}$, $R_{16}$, and $R_{17}$ are as defined above; or an unsaturated cyclic or heterocyclic compound, e.g. 1-cyclohex-1-yl methyl ether

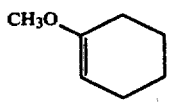

or 5,6-dihydro-4-methoxy-2H-pyran

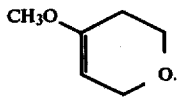

See C. B. Reese et al., J. Am. Chem. Soc. 89, 3366 (1967). The reaction conditions for such vinyl ethers and unsaturates are similar to those for dihydropyran above.

The 6-keto formula-IV compound, now with blocking groups at C-11 and C-15, is also accompanied by hemi-ketal compounds derived from formula XX but now blocked at C-11 and C-15. It is possible that the C-6 hydroxyl is also reactive to the blocking agent. Whether or not the C-6 hydroxyl is blocked is immaterial to the success of the following step (b). Any ether groups at C-6 are readily removed in the presence of the reagents used in step (b). Any hemi-ketal therefore equilibrates readily and rapidly to the 6-keto compound IV and is transformed to the formula-V compound in step (b).

In step "b" of Chart A, the hydroxyl on the cyclopentane ring at the C-9 position of the formula-IV compound is oxidized to the oxo group of the formula-V compound.

Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize the C-9 secondary hydroxy groups of the formula-IV reactant is used. Acetone is a suitable diluent for this purpose. Reaction temperature at least as low as about 0° C. should be used. Preferred reaction temperatures are in the range 0° to −50° C. Another useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

Examples of other oxidation reagents useful for this transformation are silver carbonate on Celite (Chem. Commun. 1102 (1969)), mixtures of chromium trioxide and pyridine J. Am. Chem. Soc. 75, 422 (1953), and Tetrahedron, 18, 1351 (1962)), t-butylchromate in pyridine (Biochem. J. 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

In step "c" of Chart A, the blocking groups $R_{21}$ are replaced with hydrogen by acid hydrolysis, thereby forming product VI. General procedures are known in the art. For the tetrahydropyranyl groups, for example, the formula-V compound is contacted with methanol-HCl or with acetic acid-water-tetrahydrofuran at 40°–55° C.

Thereafter, additional compounds within the scope of formula I, such as pharmacologically acceptable salts, are optionally made from formula-VI acids by processes described herein or known in the art.

As used in the formulas of Chart A and elsewhere herein, examples of alkyl of one to 4 carbon atoms, inclusive, are methyl, ethyl, propyl, butyl, and isomeric forms thereof. Examples of alkyl of one to 7 carbon atoms, inclusive, are, in addition, pentyl, hexyl, heptyl, and isomeric forms thereof. Examples of alkyl of one to 12 carbon atoms, inclusive, are, in addition, octyl, nonyl, decyl, undecyl, dodecyl, and isomeric forms thereof. Examples of alkyl of one to 18 carbon atoms are, in addition, tridecyl, tetradecyl, pentadecyl, hexadecyl, heptadecyl, octadecyl, and isomeric forms thereof.

Examples of cycloalkyl of 3 to 10 carbon atoms, inclusive, which includes alkyl-substituted cycloalkyl, are
cyclopropyl,
2-methylcyclopropyl,
2,2-dimethylcyclopropyl,
2,3-diethylcyclopropyl,
2-butylcyclopropyl
cyclobutyl,
2-methylcyclobutyl,
3-propylcyclobutyl,
2,3,4-triethylcyclobutyl,
cyclopentyl,
2,2-dimethylcyclopentyl,
3-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.

Examples of phenylalkyl of 7 to 10 carbon atoms, inclusive, are
benzyl,
1-phenylethyl,
2-phenylethyl,
2-phenylpropyl,
4-phenylbutyl, and
3-phenylbutyl.

Examples of aralkyl of 7 to 12 carbon atoms, inclusive, are, in addition
2-(1-naphthylethyl), and
1-(2-naphthylmethyl).

Examples of phenyl substituted by one to 3 chloro or alkyl of one to 4 carbon atoms, inclusive are
p-chlorophenyl,
m-chlorophenyl,
o-chlorophenyl,
2,4-dichlorophenyl,
2,4,6-trichlorophenyl,
p-tolyl,
m-tolyl,
o-tolyl,
p-ethylphenyl,
p-tert-butylphenyl,
2,5-dimethylphenyl,
4-chloro-2-methylphenyl, and
2,4-dichloro-3-methylphenyl.

Examples of alkylene of one to 9 carbon atoms, inclusive, with one to 5 carbon atoms, inclusive, in the chain, within the scope of $C_gH_{2g}$ as defined herein, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in the chain, within the scope of C$_j$H$_{2j}$ as defined herein, are those given above for C$_g$H$_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CF$_2$.

Examples of

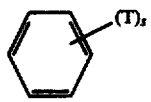

as defined herein are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-(fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-(chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl,
4- or 5-)chloro-2-methoxyphenyl, and
2,4-dichloro(5- or 6-)methoxyphenyl.

Included in the compounds of formula I are the pharmacologically acceptable salts when R$_3$ is a cation. Such pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tertamylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Salts containing pharmacologically acceptable cations are prepared from the final formula-VI compounds in free acid form, i.e. wherein R$_{19}$ is —COOH, by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula-VI acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired. Amine and quaternary ammonium salts are prepared by similar methods using appropriate solvents.

As discussed above, the compounds of formula I are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is advantageous because of increased water solubility that $R_3$ in the formula I compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration suppositories prepared as known in the art are used. For tissue implants, a sterile tablet or silicone rubber capsule or other object containing or impregnated with the substance is used.

Various esters of formula I within the scope of $R_3$ are optionally prepared from the corresponding acids of formula I, the corresponding acids of formula I, i.e. wherein $R_1$ is —COOH, by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389–394 (1954).

An alternative method for esterification of the carboxyl moiety of the novel compounds of formula I comprises transformations of the free acid to the corresponding silver salt, followed by interaction of that salt with an alkyl iodide. Examples of suitable iodides are methyl iodide, ethyl iodide, butyl iodide, isobutyl iodide, tertbutyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the formula I compounds are prepared by silylating the acid to protect the hydroxy groups, for example, replacing each —OH with —O—Si—$(CH_3)_3$. Doing that may also change —COOH to —COO—Si—$(CH_3)_3$. A brief treatment of the silylated compound with water will change —COO—Si—$(CH_3)_3$ back to —COOH. Procedures for this silylation are known in the art and are available. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—$(CH_3)_3$ are changed back to —OH by treatment with dilute acetic acid. Procedures for these transformations are known in the art.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See for example U.S. Pat. No. 3,984,454, German Offenlag. No. 2,535,693, and Derwent Farmdoc No. 16828X.

Compounds in which $R_1$ is

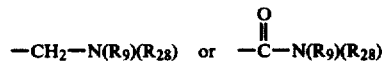

are conveniently prepared from the formula-VI products which are acids, i.e. $R_1$ is —COOH. The sequence of reactions is described hereinafter in the section on "2-Decarboxy-2-amino PGF Compounds". For example, the acid compound is converted to a mixed anhydride and thence to an amide. Carboxyl reduction of the amide yields the amine. Alternatively the mixed anhydride is converted to an azide, thence to a urethane from which the substituted amines, primary or secondary, are readily available by methods known in the art.

Also included in the compounds of this invention are the lower alkanoates, wherein "lower alkanoate" refers to an ester of an alkanoic acid of one to 8 carbon atoms, inclusive. Examples of such alkanoic acids are formic, acetic, propanoic, butanoic, pentanoic, hexanoic, heptanoic, and octanoic acids, and isomeric forms thereof.

The formula-VI compounds prepared by the process described above are transformed to lower alkanoates by interaction with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 1,000 moles of anhydride per mole of the hydroxy compound. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride. For acetic anhydride, pyridine, and a 25° C. reaction temperature, a 12-to-24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

Another process for the formula-I 6-keto compounds comprises the steps of starting with a halo ether of the formula

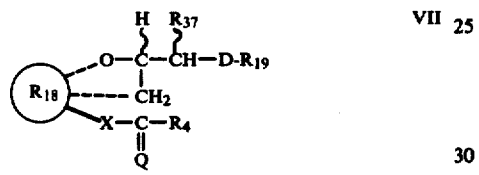

and (a) transforming that starting material to a compound of the formula

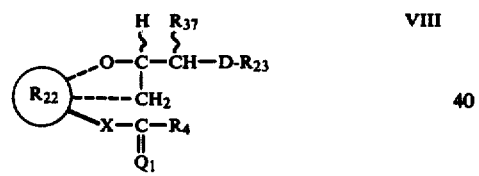

(b) subjecting the product of step "a" to dehydrohalogenation and hydrolysis to form a compound of the formula

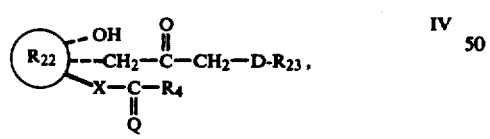

(c) oxidizing the product of step "b" to a compound of the formula

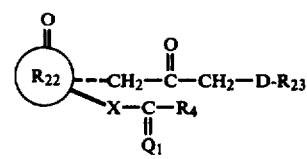

and (d) hydrolyzing the product of step "c" to form a compound of the formula

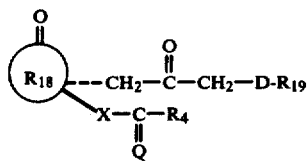

Thereafter, salts within the scope of formula I are prepared from formula-VI acids.

Chart B, herein, shows the steps of this process. The starting materials of formula VII are not the subject of this invention but will be described below.

CHART B

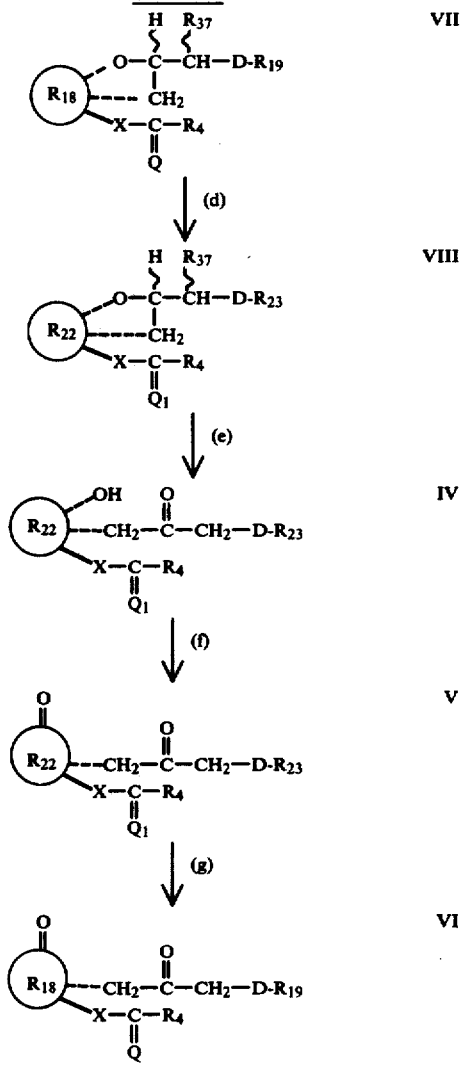

In the first step "d" of Chart B, the starting material VII is transformed to a corresponding formula-VIII compound. The blocking group $R_{21}$ in Q', $R_{22}$, and $R_{23}$ may be the same as or different than the blocking group $R_{21}$ in Chart A, but the details as to reagents and procedures have already been described above for Chart A, step "a".

In step "e" of Chart B, the formula-VIII halo compound is subjected to dehydrohalogenation and hydrolysis to form the formula IV 6-keto PGF-type compound. In one method a halo compound VIII is contacted with silver carbonate and perchloric acid in an organic medium such as tetrahydrofuran. The reaction is followed with TLC (thin layer chromatography) to determine completion, normally 15–24 hr. at about 25° C. The reaction is preferably done in absence of light.

In another method the halo compound VIII is treated with a dehydrohalogenation reagent known in the art. See for example Fieser and Fieser "Reagents for Organic Synthesis", p. 1308, John Wiley and Sons, Inc., New York, N.Y. (1967). Useful for this purpose are tertiary amines, preferably.

1,5-diazabicyclo[4.3.0]nonene-5 ("DBN")
1,4-diazabicyclo[2.2.2]octane ("DABCO") and
1,5-diazabicyclo[5.4.0]undecene-5("DBU").

The reaction is carried out in an inert medium such as dimethylformamide and is followed by TLC, to show the disappearance of starting material. The reaction proceeds at 25° C. and can be accelerated at 40°–50° C. An intermediate enol ether is thereby obtained, preferably purified by washing free of amine, and thereafter treated with dilute aqueous acid, preferably acetic acid, until the more polar formula-IV compound is formed as shown by TLC.

The formula-IV 6-keto compounds are in equilibrium with and therefore accompanied by hemi-ketals of the formula

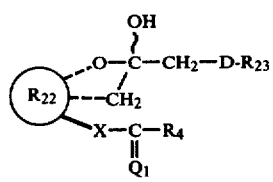

XXI

Such hemi-ketals equilibrate rapidly to the 6-keto compound IV during the oxidation and are transformed to the formula-V compound in step (f).

Thereafter in steps "f" and "g" the product above is oxidized to the formula-V compound, and finally hydrolyzed to yield the formula-VI product. The reagents and conditions for these steps have already been described above for Chart A, steps "b" and "c".

There is further disclosed a process for preparing 6-keto-13,14-didehydro-PGE-type compounds of the formula

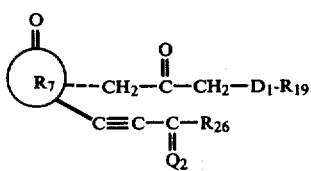

X which comprises the steps of starting with a compound of the formula

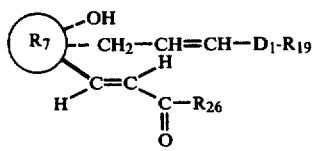

XI and (a) subjecting that starting material to selective halogenation and selective monodehydrohalogenation to form a 5,6,14-trihalo compound represented by the formula

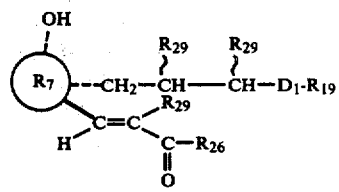

XII (b) subjecting the product of step "a" to reduction to form a compound of the formula

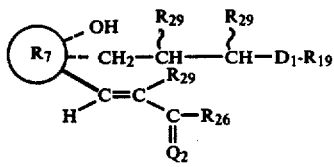

XIII (c) subjecting the product of step (b) to selective dehalogenation to form a compound of the formula

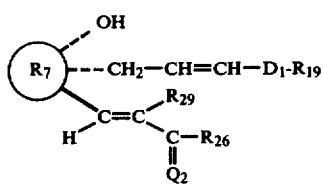

XIV (d) halogenating and cyclizing to form a compound of the formula

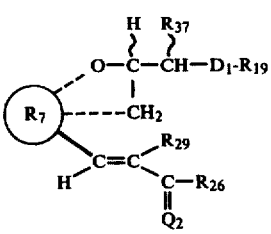

XV (e) transforming the product of step "d" to a compound of the formula

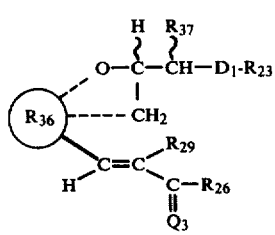

XVI (f) transforming the product of step "e" to a compound of the formula

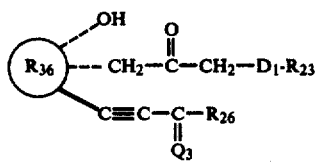

(g) subjecting the product of step (f) to oxidation to form a compound of the formula

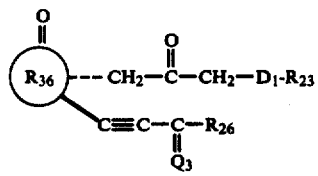

(h) hydrolyzing the product of step "g" to replace the blocking groups $R_{21}$ with hydrogen and thereby form 6-keto-13,14-didehydro PGE-type compounds of formula X.

Chart C, herein, shows the steps of that process. The starting materials of formula XI are 15-oxo PGF type compounds known in the art or available by methods described herein or known in the art. For example see U.S. Pat. No. 3,728,382. It is immaterial whether 5,6-cis or 5,6-trans compounds are used as either one will ultimately yield the desired formula-X compound.

CHART C

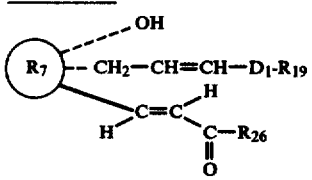

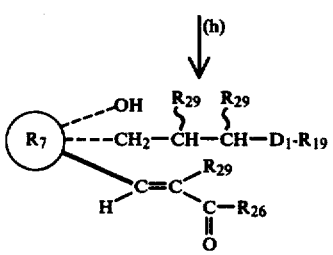

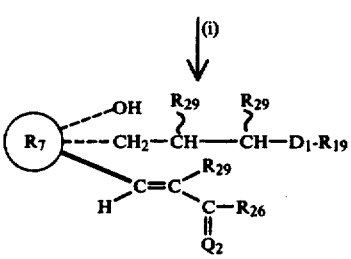

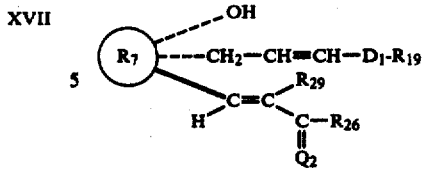

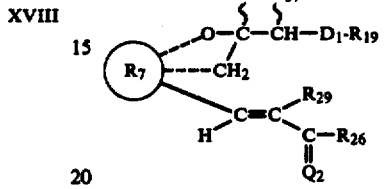

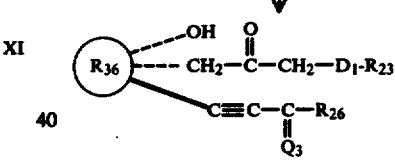

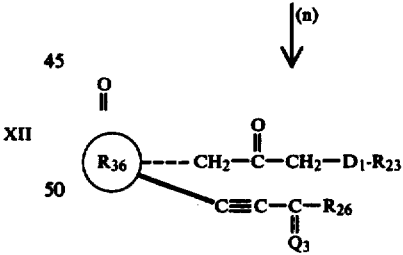

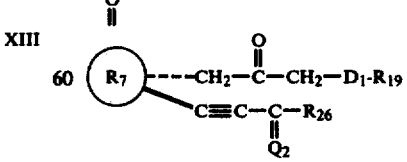

In the first step "h" of Chart C the formula-XII trihalo compound is prepared, for example by reaction of the formula-XI compound with pyridinium hydrobromide perbromide in pyridine. Other halogenating agents are useful, e.g. N-bromo- or N-chloro-succinimide. Other tertiary amines are useful for the selective monodehydrohalogenation.

In step "i", the formula-XIII compound is obtained as a mixture of alpha and beta hydroxy isomers by reduction of XII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, or diisobutyl aluminum hydride. For production of the preferred natural-configuration prostaglandin derivatives, the alpha form of the formula-XIII compound is separated from the beta isomer by silica gel chromatography using methods known in the art.

In step "j" the C-5 and C-6 halogen atoms are removed by selective dehalogenation for example by contact with zinc in methanolic ammonium chloride, to yield the formula-XIV monohalo compound. Other monohalo compounds within the scope of XIV are known in the art. See for example U.S. Pat. No. 4,029,681.

In step "k" the formula-XIV compound is halogenated and cyclized to form the formula-XV halo ether. For this purpose there are various methods available. For the iodo compounds there may be used an aqueous system containing iodine, potassium iodide, and an alkali carbonate or bicarbonate, or an organic solvent system such as dichloromethane containing iodine in the presence of an alkali metal carbonate. The reaction is carried out at temperatures below 25° C., preferably about 0°–5° C. for 10–20 hours. Thereafter the reaction is quenched with sodium sulfite and sodium carbonate and the formula-XV compound separated from the reaction mixture.

For the bromo compounds, N-bromosuccinimide or N-bromoacetamide are useful. See Fieser et al., Reagents for Organic Synthesis, Vol. 1, pp. 74 and 78, Vol. IV, p. 51, John Wiley and Sons, Inc., N.Y. For the chloro compound various methods are available, for example exchange of bromo with chloro using the silver salt of chlorodifluoroacetic acid. See I. T. Harrison et al., Compendium of Organic Synthetic Methods, p. 346, 1971, Wiley Interscience, N.Y.

The formula-XV halo compounds are obtained as two isomers, one in minor and the other in major quantity, differing in their chromatographic mobility. These C-5 and C-6 isomers are separable by silica gel chromatography, but are normally not separated, as either one yields the desired formula XVII, XVIII, and X compounds.

In step "l" the formula-XVI compound is formed as known in the art or described herein, replacing hydrogen atoms in free hydroxyls in $Q_2$, $R_{19}$, and $R_7$ with blocking groups $R_{21}$.

In step "m" the formula-XVI compound is treated with a dehydrohalogenation reagent preferably potassium t-butoxide, to form the formula-XVII 6-keto-PGF-type compound.

The remaining steps in the process, "n" and "o", are analogous to those in Chart A. For step "n", the formula-XVII compound is subjected to oxidation as in step "b" of Chart A. In step "o" the formula-XVIII compound is hydrolyzed to remove blocking groups as in step "c" of Chart A.

Referring now to Chart D, there is shown a source of the formula-III 6-keto-PGF$_{1\alpha}$-type starting materials for Chart A and the formula-VII halo ether starting materials for Chart B.

CHART D

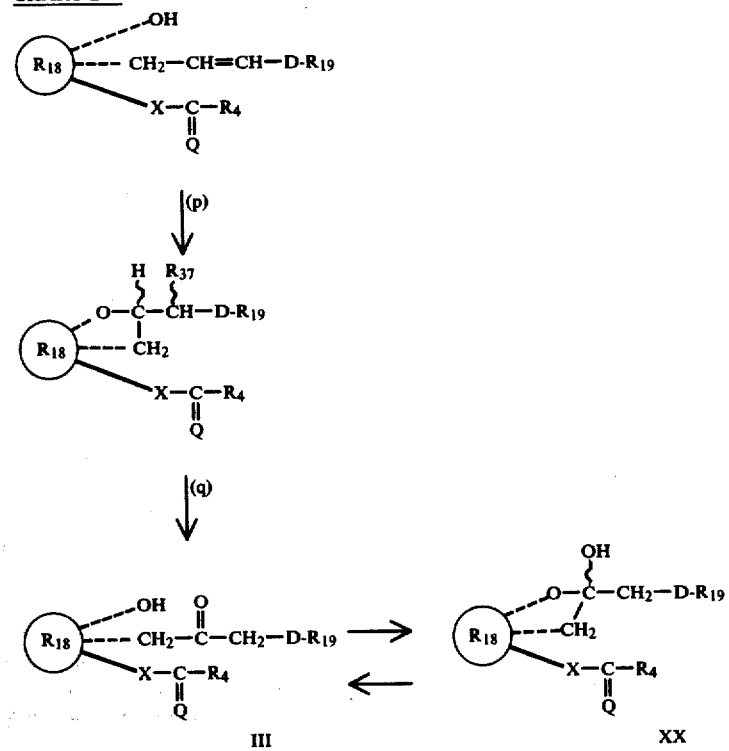

The starting materials of formula XIX are known in the art or are readily available by processes known in the art. For example, as to PGF$_{2\alpha}$ see U.S. Pat. No. 3,706,789; as to 15-methyl- and 15-ethyl-PGF$_{2\alpha}$, see U.S. Pat. No. 3,728,382; as to 16,16-dimethyl-PGF$_{2\alpha}$, see U.S. Pat. No. 3,903,131; as to 16,16-difluoro-PGF$_{2\alpha}$ compounds, see U.S. Pat. Nos. 3,962,293 and 3,969,380; as to 16-phenoxy-17,18,19,20-tetranor-PGF$_{2\alpha}$, see Derwent Farmdoc No. 73279U; as to 17-phenyl-18,19,20-trinor-PGF$_{2\alpha}$, see Derwent Farmdoc No. 31279T; as to 11-deoxy-PGF$_{2\alpha}$, see Derwent Farmdoc No. 10695V; as to 2a,2b-dihomo-PGF$_{2\alpha}$, see Derwent Farmdoc No. 61412S and U.S. Pat. Nos. 3,852,316 and 3,974,159; as to 3-oxo-PGF$_{2\alpha}$, see U.S. Pat. No. 3,923,861; as to 3-oxa-17-phenyl-18,19,20-trinor-PGF$_{2\alpha}$, see U.S. Pat. No. 3,931,289; as to substituted phenacyl esters, see Derwent Farmdoc No. 16828X; as to substituted phenyl esters, see U.S. Pat. No. 3,890,372; as to C-1 alcohols, i.e. 2-decarboxy-2-hydroxymethyl compounds, see U.S. Pat. No. 3,636,120; as to C-2 tetrazolyl derivatives, see U.S. Pat. No. 3,932,389; as to Δ2-PGF$_{2\alpha}$ see Derwent Farmdoc No. 46497W and Ger. Offen. No. 2,460,285; as to 5,6-trans-PGF$_{2\alpha}$, see U.S. Pat. No. 3,759,978; as to 2,2-dimethyl-PGF$_{2\alpha}$ analogs, see Derwent Farmdoc No. 59033T and Ger. Offen. No. 2,209,039; as to 11β-PGF$_{2\alpha}$ compounds, see U.S. Pat. No. 3,890,371; as to 11-deoxy-PGF$_{2\alpha}$, see Derwent Farmdoc No. 10695V; as to 11-deoxy-11-hydroxymethyl-PGF$_{2\alpha}$, see U.S. Pat. Nos. 3,931,282 and 3,950,363; as to 16-methylene-PGF$_{2\alpha}$, see Derwent Farmdoc No. 19594W and Ger. Offen. No. 2,440,919; as to 17,18-didehydro-PGF$_{2\alpha}$ compounds, see U.S. Pat. No. 3,920,726; as to 3-(or 4-)oxa-17,18-didehydro-PGF$_{2\alpha}$ compounds, see U.S. Pat. No. 3,920,723; as to 15-oxo-PGF$_{2\alpha}$, see U.S. Pat. No. 3,728,382; as to 15-deoxy-PGF$_{2\alpha}$, see Derwent Farmdoc No. 9239W; as to 13,14-cis compounds, see U.S. Pat. No. 3,932,479; as to 11-deoxy-15-deoxy-PGF$_{2\alpha}$ see Derwent Farmdoc No. 5694U; as to ω-homo-PGF$_{2\alpha}$ compounds, see Derwent Farmdoc No. 4728W; and as to 2,2-difluoro-PGF$_{2\alpha}$ compounds, see Derwent Farmdoc No. 67438R.

As to 2-decarboxy-2-amino-PGF$_{2\alpha}$ compounds, see that section incorporated herein, taken from a prior-filed, commonly-owned U.S. patent application.

In step "p" of Chart D, the starting material XIX is subjected to halogenation and cyclization to yield the formula-VII halo compounds. For this purpose there is used any of the halogenating methods described above for step "k" of Chart C. Here also it is immaterial whether 5,6-cis or 5,6-trans compounds of formula-XIX are used or which isomers of the formula-VII halo compounds are used.

In step "q" of Chart D the halo compound is converted to the mixture of compounds III and XX by dehydrohalogenation and hydrolysis. See for example the methods of Chart B, step "e" above.

CHART E

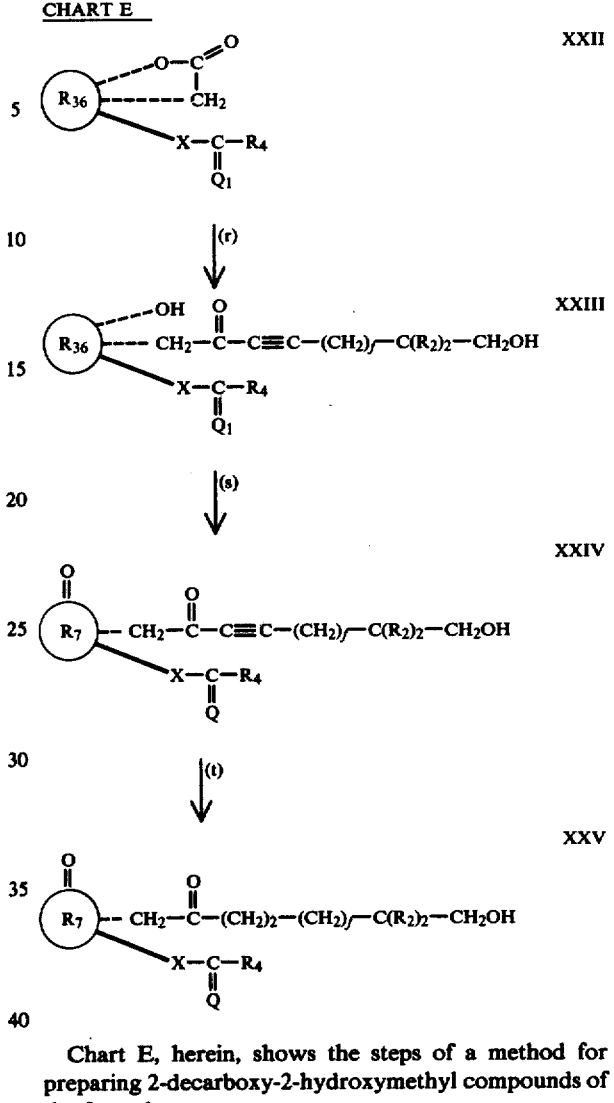

Chart E, herein, shows the steps of a method for preparing 2-decarboxy-2-hydroxymethyl compounds of the formula

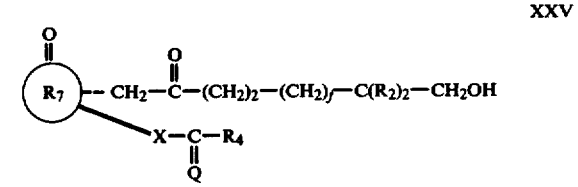

The formula-XXII starting materials for Chart E are lactone intermediates known in the art or readily available by methods known in the art. For example when R$_{36}$ is

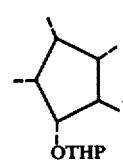

(THP = tetrahydropyran-2-yl)

and when R4 is n-pentyl, see Corey et al., J. Am. Chem. Soc. 92, 397 (1970). When R4 is

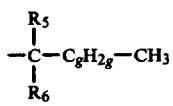

wherein R5 and R6 are methyl or ethyl, see U.S. Pat. No. 3,954,833. When R5 and R6 are fluoro, see U.S. Pat. No. 3,962,293. When Q1 is

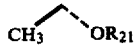

see U.S. Pat. No. 3,864,387 and 3,931,279.
When (R36) is

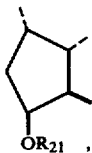

these 11β lactones are obtained by isomerizing a corresponding lactone having the 11α configuration, with suitable blocking at the C-15 position if desired, by methods known in the art, such as by way of the 11-mesylate or 11-tosylate.
When (R36) is

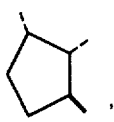

and R4 is alkyl, see U.S. Pat. No. 3,931,279 and Derwent Farmdoc Abstract No. 10695V; when R4 is phenyl-substituted, also see U.S. Pat. No. 3,931,279.
When (R36) is

see Ger. Offen. No. 2,437,622 and Derwent Farmdoc No. 12714W. For example a compound of the formula

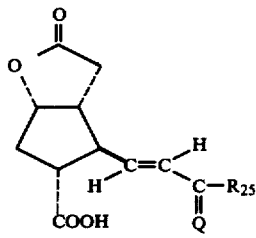

XXVI is reduced at the —COOH position to the corresponding —CH2OH compound using diborane, and thereafter reacted with a suitable blocking agent.

In step "r" of Chart E the starting material XXII is condensed with an alkyllithium compound of the formula

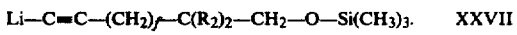

XXVII

See C. H. Lin et al. Synthetic Comm. 6, 503 (1976) and Lin J. Org. Chem. 41, 4045 (1976). The lithium compound is conveniently prepared in situ from the silylated alkyne by reaction with methyl- or butyllithium in an ether such as diethylether or tetrahydrofuran. In working up the product the silyl groups are readily removed to yield XXIII.

In step "s" the formula-XXIII compound is oxidized at the C-9 position, preferably with Jones reagent. In this step some of the C-1 alcohol groups are also oxidized to carboxylic acid groups. These are next methylated with diazomethane to facilitate removal of the by-product by chromatography. Blocking groups R21 are replaced with hydrogen in the conventional way, as by mild acid hydrolysis for THP, to yield the formula-XXIV compound.

In step "t" compound XXIV is reduced to the XXV compound without reducing $C_{13}$-$C_{14}$ or $C_{17}$-$C_{18}$ ethylenic bonds that are present. For this purpose catalytic hydrogenation is useful, for example, over palladium on barium sulfate.

Chart F, herein, shows the steps of a method for preparing 6,15-di keto compounds of the formula

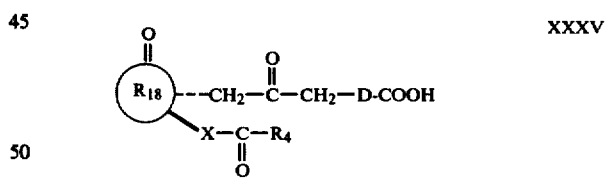

XXXV

The starting material is an equilibrium mixture of the formula-XXVIII 6-keto-PGF$_{1\alpha}$-type and formula-XXIX hemiketal compounds. See for example Johnson et al. J. Am. Chem. Soc. 99, 4182 (1977).

CHART F

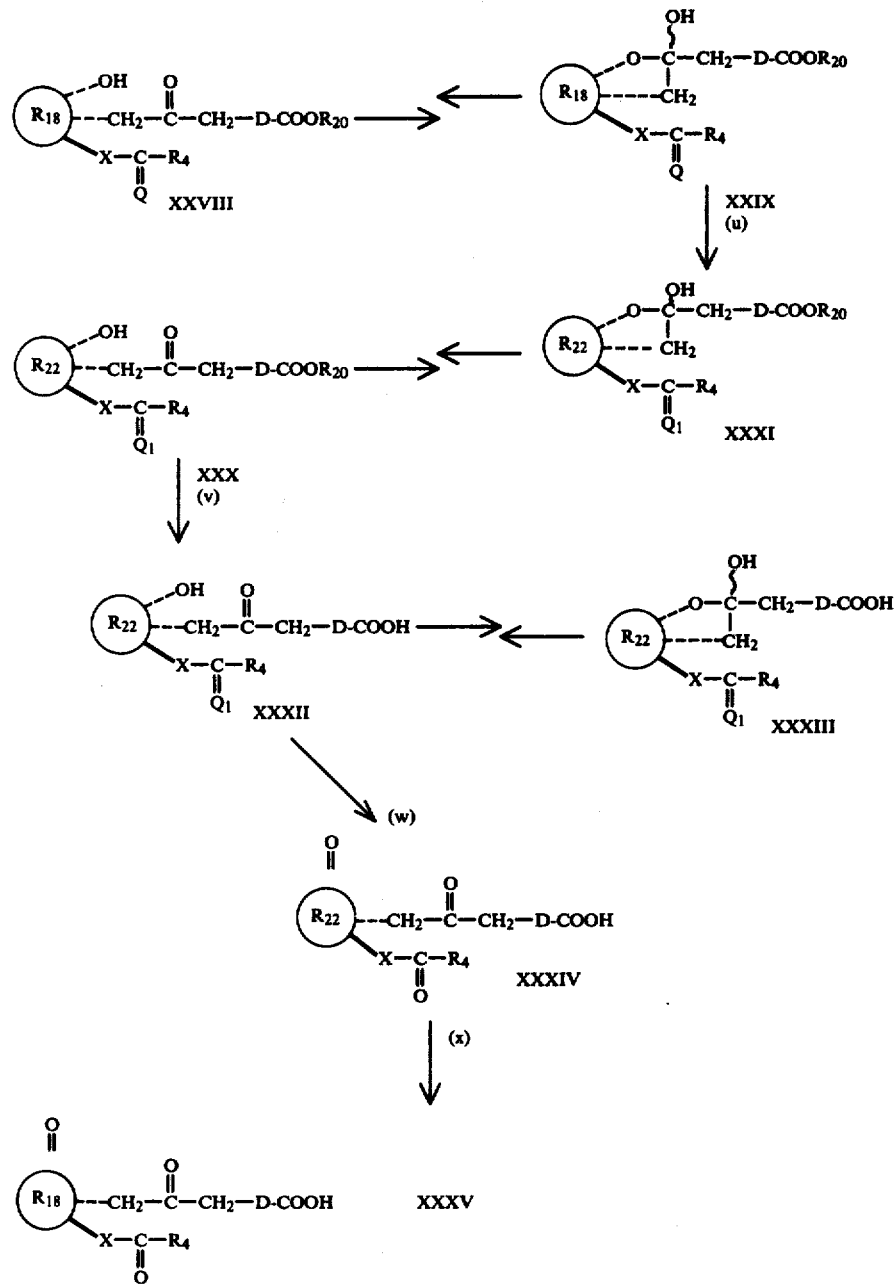

In step "u", the blocking groups $R_{21}$ are added, using methods described herein or known in the art. With dihydropyran, for example, the main product is the bis(THP ether).

In step "v" the free acid is formed by saponification of the carboxylic ester groups and acidification.

In step "w" the blocked 6-keto-PGF$_{1\alpha}$-type compound of formula XXXII is oxidized, for example with Jones reagent, to the formula-XXXIV 6,15-diketo-PGE$_1$-type compound.

Finally, the step "x" the blocking groups are removed in the conventional way to obtain the formula-XXXV product.

CHART G

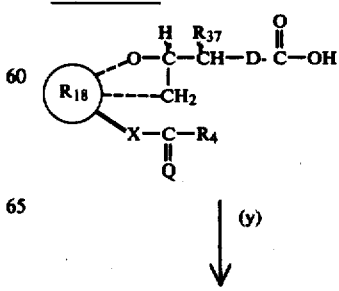

XXXVI

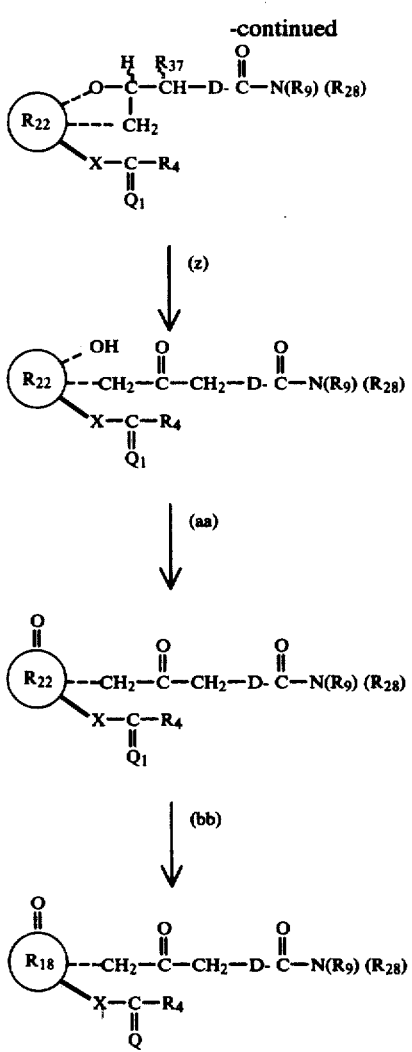

Chart G shows the steps in a preferred method for preparing amides of the formula

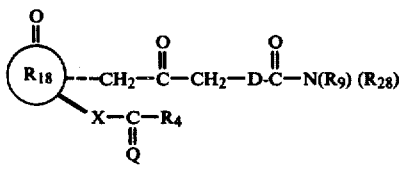

XL

The starting materials of formula XXXVI are 5-halo acids within the scope of formula VII of Chart B herein.

In step "y" the formula-XXXVI halo acid is converted to amide XXXVII, e.g. by way of a mixed anhydride. For this purpose, compound XXXVI is treated with isobutyl chloroformate in the presence of a tertiary amine such as triethylamine and thereafter with an amine of the formula $HN(R_9)(R_{28})$.

In step "z" the halo amide XXXVII is then subjected to dehydrohalogenation and hydrolysis to obtain the formula-XXXVIII compound. Silver carbonate and perchloric acid are useful for this purpose.

In step "aa" the formula-XXXVIII 6-keto-$PGF_{1\alpha}$-type compound, having suitable blocking groups at C-11 and C-15, is oxidized to a $PGE_1$-type compound by methods known in the art, for example using Jones reagent at about $-15°$ to $-20°$ C.

Finally, in step "bb" the blocking groups are removed, to produce compound XL.

It should be understood that although the Charts have formulas drawn with a specific configuration for the reactants and products, the procedural steps are intended to apply not only to the other optically active isomers, but also to mixtures, including racemic mixtures or mixtures of enantiomeric forms.

If optically active products are desired, optically active starting materials or intermediates are employed or, if racemic starting materials or intermediates are used, the products are resolved by methods known in the art for prostaglandins.

The products formed from each step of the reaction are often mixtures and, as known to one skilled in the art, may be used as such for a succeeding step or, optionally, separated by conventional methods of fractionation, column chromatography, liquid-liquid extraction, and the like, before proceeding.

Compounds within the scope of formula I are transformed from one to another by methods known in the art. Accordingly, a formula-I compound wherein

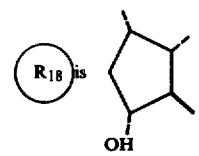

is transformed to another formula-I compound wherein $R_{18}$ is another ring within the scope of $R_{18}$, for example an 11-deoxy compound, by methods known or described herein. A compound wherein

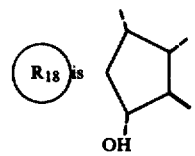

is transformed to one wherein

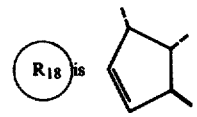

by acid dehydration. A compound wherein the $C_{13}-C_{14}$ group "X" is trans—CH=CH— is transformed by known methods to another compound wherein the $C_{13}-C_{14}$ group is cis—CH=CH—, —C≡C—, or —$CH_2CH_2$—. For example, —C≡C— is obtained by selective bromination and dehydrobromination. A compound wherein the $C_2$ substituent is —$COOR_3$, e.g. a methyl ester, is transformed by known methods to another compound having another $C_2$ substituent within the scope of $R_1$, as defined herein, for example —$CH_2OH$ or

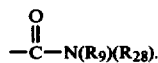

Compounds of formula V (Chart A), XVIII (Chart C), XXIV (Chart E), XXXIV (Chart F), and XXXIX (Chart G) having blocking groups are useful as intermediates in the various processes for preparing other useful compounds as described herein or known in the art.

To obtain the optimum combination of biological response specificity, potency, and duration of activity, certain compounds within the scope of formula I are preferred. For example it is preferred that Q be

wherein it is especially preferred that $R_8$ be hydrogen, or methyl.

When Q is

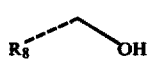

it is preferred that $R_8$ is methyl.

Another preference for the compounds of formula I, as to $R_1$, is that $R_3$ in —COOR$_3$ be either hydrogen or alkyl of one to 12 carbon atoms, inclusive, or a salt of a pharmacologically acceptable cation. Further, when $R_3$ is alkyl, it is more preferred that it be alkyl of one to 4 carbon atoms, and especially methyl or ethyl.

For purposes of stability on long storage it is preferred for the compounds of formula I that $R_3$ in —COOR$_3$ be amido-substituted phenyl or phenacyl as illustrated herein.

For oral administration of compounds I it is preferred that $R_1$ be

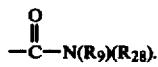

It is especially preferred that at least one of $R_9$ and $R_{28}$ be hydrogen.

As to variations in D, it is preferred that "d" be 2, 3, or 4, and especially 2. When both $R_2$'s are fluoro, it is preferred that $R_8$ in Q be methyl, or that $R_4$ be

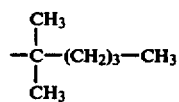

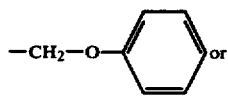

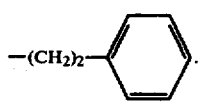

As to variations in $R_{18}$, it is preferred that $R_{18}$ be

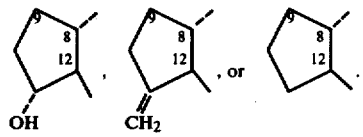

When $R_4$ in the compounds of formula I is $$-\underset{R_6}{\overset{R_5}{\underset{|}{\overset{|}{C}}}}-C_gH_{2g}-CH_3,$$

it is preferred that $C_gH_{2g}$ be alkylene of 2, 3, or 4 carbon atoms, and especially that it be trimethylene. It is further preferred that $R_5$ and $R_6$ be hydrogen, methyl, ethyl, or fluoro, being the same or different. It is further preferred, when $R_5$ and $R_6$ are not hydrogen, that both $R_5$ and $R_6$ be methyl or fluoro. It is especially preferred that $R_4$ be n-pentyl, 1,1-dimethylpentyl, or 1,1-difluoropentyl.

When $R_4$ in the compounds of formula I is

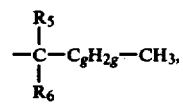

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_4$ be

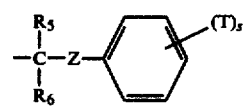

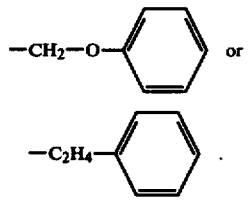

With respect to Chart H a method is provided whereby the formula CI $PGF_{2\alpha}$- or 11-deoxy-$PGF_{2\alpha}$-type free acid is transformed to the various 2-decarboxy-2-aminomethyl or 2-decarboxy-2-(substituted amino)methyl-$PGF_\alpha$- or 11-deoxy-$PGF_\alpha$-type compounds of formulas CIV, CVI, CVII, CVIII, CIX, or CX.

By the procedure of Chart H the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type, azide.

For preparation of the PGF$_{2\alpha}$-type, amide (formula CIII) the formula CII mixed acid anhydride is reacted with liquid ammonia or ammonium hydroxide.

Alternatively, the formula CIII compound is prepared from the formula CI free acid by methods known in the art for transformation to carboxy acids to corresponding carboxyamides. For example, the free acid is transformed to a corresponding methyl ester (employing methods known in the art; e.g., excess etheral diazomethane), and a methyl ester thus prepared is transformed to the formula CIII amide employing the methods described for the transformation of the formula CII mixed acid anhydride to the formula CIII amide.

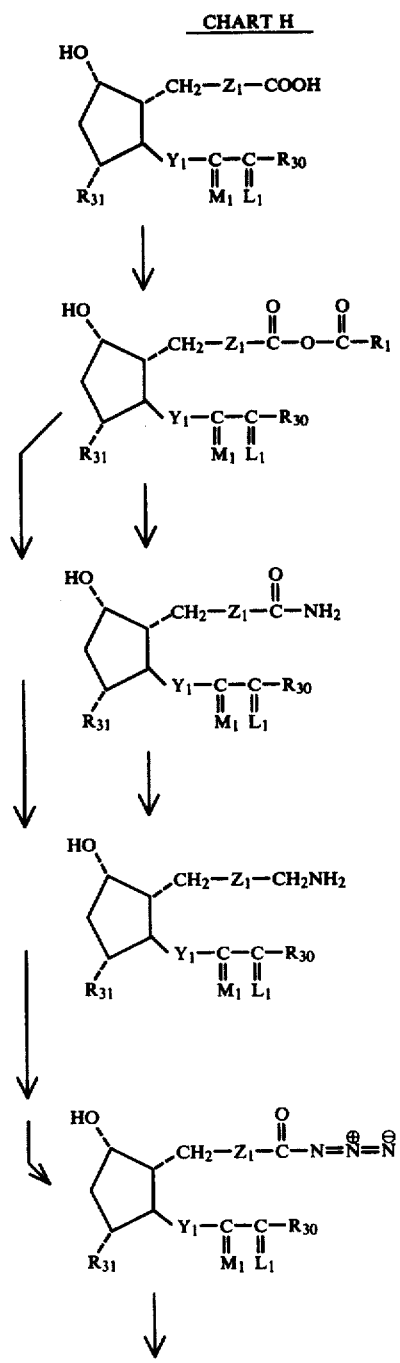

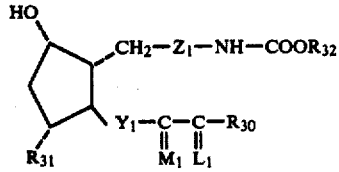

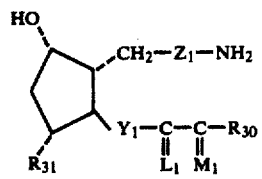

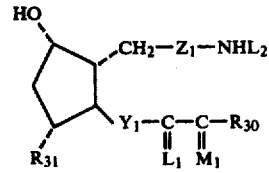

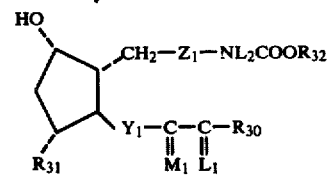

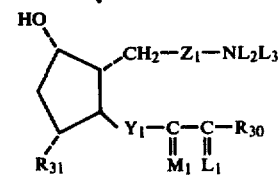

Thereafter the formula CIV 2-decarboxy-2-aminomethyl-PGF$_{2\alpha}$- or 11-deoxy-PGF$_{2\alpha}$-type compound is prepared from the formula CIII compound by carbonyl reduction. Methods known in the art art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041-1043, wherein reagents and reaction conditions for the azide formation are discussed.

Finally, the formula CVI urethane is prepared from the formula CV azide reaction with an alkanol, aralkanol, phenol or substituted phenol. For example, when methanol is employed the formula CVI compound is prepared wherein $R_{32}$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium potassium or lithium hydroxide is employed.

Alternatively, the formula CVI compound is employed in the preparation of the formula CVIII compound. Thus, when $L_1$ is alkyl the formula CVIII compound is prepared by reduction of the formula CVI urethane wherein $R_{32}$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondard amines. Finally, the formula CX product wherein $L_2$ and $L_3$ are both alkyl is prepared by reduction of the formula CIX cabamide. Accordingly, methods hereinabove described for the preparation of the formula CVIII compound from the formula CVI compound are used. Optionally, the various reaction steps herein may be preceded by the employment of blocking groups according to $R_{21}$, thus necessitating their subsequent hydrolysis in preparing each of the various products above. Methods described hereinabove for the introduction and hydrolysis of blocking groups according to $R_{21}$ are employed.

Finally, the processes described above for converting the formula CII compound to the formula CV compound and the various compounds thereafter, result in shortening the 8a-side chain of the formula CI compound by one carbon atom. Accordingly, the formula CI starting material should be selected so as to compensate for the methylene group which is consumed in the steps of the above synthesis. Thus, where a 2a-homo-product is desired a corresponding formula Cl 2a,2b-dihomo starting material must be employed.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer in deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"DBN", herein, refers to 1,5-diazabicyclo[4.3.0]nonene-5.

"DABCO", herein, refers to 1,4-diazabicyclo[2.2.2]-octane.

"DBU", herein, refers to 1,5-diazabicyclo[5.4.0]undecene-5.

"DIBAL", herein, refers to diisobutylaluminum hydride.

"E" and "Z", herein, follow Blackwood et al., cited above. "Florisil®", herein, is a chromatographic magnesium silicate produced by the Floridin Co. See Fieser et al. "Reagents for Organic Synthesis" p. 393 John Wiley and Sons, Inc., New York, N.Y. (1967).

"HPLC", herein, refers to high pressure liquid chromatography.

"Skellysolve B", herein, refers to mixed isomeric hexanes.

"THP", herein, refers to tetrahydropyran-2-yl.

"TLC", herein refers to thin layer chromatography.

"Concentrating", as used herein, refers to concentration under reduced pressure, preferably at less than 50 mm. and at temperatures below 35° C.

"Drying", as used herein, refers to contacting a compound, in solution, with an anhydrous agent such as sodium sulfate or magnesium sulfate to remove water and filtering to remove solids.

Silica gel chromatography, as used herein, is understood to include elution, collection of fractions, and combination of those fractions shown by TLC to contain the desired product free of starting material and impurities.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 247 (1966).

Preparation 1

5ξ-Iodo-9-deoxy-6,9-epoxy-PGF$_{1\alpha}$, Methyl Ester (Formula VII D is —(CH$_2$)$_3$—, Q is

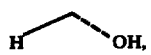

$R_4$ is n-pentyl,

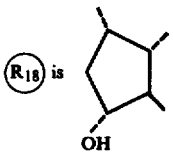

$R_{19}$ is —COOCH$_3$, and X is trans—CH=CH—.)

Refer to Chart D. A suspension of PGF$_{2\alpha}$, methyl ester as its 11,15-bis(tetrahydropyranyl)ether (2.0 g.) in 23 ml. of water is treated with sodium bicarbonate (0.7 g.) and cooled in an ice bath. To the resulting solution is added potassium iodide (1.93 g.) and iodine (2.82 g.) and stirring continued for 16 hr. at about 0° C. Thereafter a solution of sodium sulfite (1.66 g.) and sodium carbonate (0.76 g.) in 10 ml. of water is added. After a few minutes the mixture is extracted with chloroform. The organic phase is washed with brine, dried over sodium sulfate, and concentrated to yield mainly the bis(tetrahydropyranyl) ether of the title compound, 2.2 g., an oil. Hydrolysis of this ether in acetic acid-water-tetrahydrofuran (20:10:3) yields mainly the title compound, which is further purified by silica gel chromatography. $R_f$ 0.20 (TLC on silica gel in acetonedichloromethane (30:70)). The mass spectral peaks for the formula-VII compound (TMS derivative) are at 638, 623, 607, 567, 548, 511, and 477.

Following the procedures of Preparation 1, as illustrated in Chart D, but replacing the formula-XIX starting material with the following formula-XIX compounds or C-11 derivatives within the scope of formula XIX:
15-Methyl-PGF$_{2\alpha}$
(15R)-15-Methyl-PGF$_{2\alpha}$
15-Ethyl-PGF$_{2\alpha}$
16,16-Dimethyl-PGF$_{2\alpha}$
16,16-Difluoro-PGF$_{2\alpha}$
16-Phenoxy-17,18,19,20-tetranor-PGF$_{2\alpha}$
17-Phenyl-18,19,20-trinor-PGF$_{2\alpha}$
11-Deoxy-PGF$_{2\alpha}$
2a,2b-Dihomo-PGF$_{2\alpha}$
3-Oxa-PGF$_{2\alpha}$
3-Oxa-17-phenyl-18,19,20-trinor-PGF$_{2\alpha}$
there are obtained the corresponding formula-VII iodo compounds.

Preparation 2

6-Keto-PGF$_{1\alpha}$, Methyl Ester (Formula III, D, Q, R$_4$, R$_{18}$, R$_{19}$, and X as defined in Preparation 1).

Refer to Chart D. A solution of the formula-VII iodo compound, methyl ester (Preparation 1, 0.45 g.) in 20 ml. of tetrahydrofuran is treated with silver carbonate (0.250 g.) and perchloric acid (70%, 0.10 ml.), and stirred at about 25° C. for 24 hr. The mixture is diluted with 25 ml. of ethyl acetate and the organic phase is washed with saturated sodium carbonate solution and brine, dried, and concentrated to an oil, 0.41 g. Separation by silica gel chromatography eluting with ethyl acetate-Skellysolve B (3:1) yields the formula-III title compound as a more polar material than the formula-VII starting material. The product is an oil, 0.32 g., having $R_f$ 0.38 (TLC on silica gel in acetonedichloromethane (1:1)); infrared spectral peak at 1740 cm$^{-1}$ for carbonyl; NMR peaks at 5.5, 3.2–4.8, 3.7, 2.1–2.7δ.

Preparation 3

5ξ-Iodo-9-deoxy-6ξ,9α-epoxy-PGF$_1$, Mixed Isomers (Formula VII) and 9-Deoxy-6ξ,9α-epoxy-6ξ-hydroxy-PGF$_1$ (Formula XX) and 6-keto-PGF$_{1\alpha}$ (Formula III).

A solution of the formula-VII iodo compound methyl ester (Preparation 1, 1.0 g.) in 30 ml. of methanol is treated with 20 ml. of 3 N aqueous potassium hydroxide at about 0° C. for about 5 min., then at about 25° C. for 2 hr. The mixture is acidified with 45 ml. of 2 N potassium acid sulfate and 50 ml. of water to pH 1.0, saturated with sodium chloride and extracted with ethyl acetate. The organic phase is washed with brine, dried over sodium sulfate and concentrated to an oil, 1.3 g. The oil is subjected to silica gel chromatography, eluting with acetone-dichloromethane (30:70 to 50:50) to yield, first the formula-VII free acid compound and later, the mixed formula-III and -XX compounds as a more polar fraction.

The formula-VII compound is an oil, 0.33 g., having $R_f$ 0.33 (TLC on silica gel in acetone-dichloromethane (1:1) plus 2% acetic acid), $[\alpha]_D = +20°$ (C=0.992 in chloroform), infrared spectral peaks at 3360, 2920, 2860, 2640, 1730, 1710, 1455, 1410, 1380, 1235, 1185, 1075, 1050, 1015, 970, and 730 cm$^{-1}$, and mass spectral peaks (TMS derivative) at 696.2554, 681, 625, 606, 569, 535, 479, and 173.

The mixture of 9-deoxy-6ξ,9α-epoxy-6ξ-hydroxy-PGF$_1$ and 6-keto-PGF$_{1\alpha}$ is a solid 0.113 g., melting at 93°–98° C., containing no iodine, having $R_f$ 0.13 (TLC on silica gel in acetone-dichloromethane (1:1) plus 2% acetic acid) and having mass spectral peaks (TMS derivative) at 587, 568, 553, 497, 485, 478, 407, 395,, 388, and 173.

Following the procedures of Preparations 2 and 3, but replacing the formula-VII iodo compound therein with those formula-VII iodo compounds described subsequent to Preparation 1, there are obtained the corresponding formula-III and -XX compounds.

Following the procedures of Preparations 1, 2, and 3, as described above, but employing corresponding starting materials, there are prepared the
formula-VII 9-deoxy-6,9-epoxy-5-halo-PGF$_{1\alpha}$-type compounds, including iodo, bromo, and chloro compounds,
formula-III 6-keto-PGF$_{1\alpha}$-type compounds, and
formula-XX 9-deoxy-6,9-epoxy-6-hydroxy-PGF$_{1\alpha}$-type compounds
having the following structural features:
16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;

16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
2,2-Difluoro-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethoxyphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,10-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
16-Methyl-cis-13;
16,16-Dimethyl-cis-13-;
16-Fluoro-cis-13-;
16,16-Difluoro-cis-13-;
17-Phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
16-Methyl-17-phenyl-18,19,20-trinor-cis-13-;
16,16-Dimethyl-17-phenyl-18,19,20-trinor-cis-13-;
16-Fluoro-17-phenyl-18,19,20-trinor-cis-13-;
16,16-Difluoro-17-phenyl-18,19,20-trinor-cis-13-;
16-Phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
16-Phenoxy-18,19,20-trinor-cis-13-;
16-Methyl-16-phenoxy-18,19,20-trinor-cis-13-;
2,2-Difluoro-cis-13-;
2,2-Difluoro-16-methyl-cis-13-;
2,2-Difluoro-16,16-dimethyl-cis-13-;
2,2-Difluoro-16-fluoro-cis-13-;
2,2-Difluoro-16,16-difluoro-cis-13-;
2,2-Difluoro-17-phenyl-18,19,20-trinor-cis-13-;
2,2-Difluoro-17-(m-trifluoromethylphenyl)-18,19,20-trinor-cis-13-;

2,2-Difluoro-17-(m-chlorophenyl)-18,19,20-trinor-cis-13-;
2,2-Difluoro-17-(p-fluorophenyl)-18,19,20-trinor-cis-13-;
2,2-Difluoro-16-methyl-17-phenyl-18,19,20-trinor-cis-13-;
2,2-Difluoro-16,16-dimethyl-17-phenyl-18,19,20-trinor-cis-13-;
2,2-Difluoro-16-fluoro-17-phenyl-18,19,20-trinor-cis-13-;
2,2-Difluoro-16,16-difluoro-17-phenyl-18,19,20-trinor-cis-13-;
2,2-Difluoro-16-fluoro-18-phenyl-19,20-dinor-cis-13-;
2,2-Difluoro-16,16-difluoro-18-phenyl-19,20-dinor-cis-13-;
2,2-Difluoro-16-phenoxy-17,18,19,20-tetranor-cis-13-;
2,2-Difluoro-16-(m-trifluoromethylphenoxy)-17,18,19,20-tetranor-cis-13-;
2,2-Difluoro-16-(m-chlorophenoxy)-17,18,19,20-tetranor-cis-13-;
2,2-Difluoro-16-(p-fluorophenoxy)-17,18,19,20-tetranor-cis-13-;
2,2-Difluoro-16-phenoxy-18,19,20-trinor-cis-13-;
2,2-Difluoro-16-methyl-16-phenoxy-18,19,20-trinor-cis-13-;
3-Oxa-;
3-Oxa-16-methyl-;
3-Oxa-16,16-dimethyl-;
3-Oxa-16-fluoro-;
3-Oxa-16,16-difluoro-;
3-Oxa-17-phenyl-18,19,20-trinor-;
3-Oxa-17-(m-trifluoromethylphenyl)-18,19,20-trinor-;
3-Oxa-17-(m-chlorophenyl)-18,19,20-trinor-;
3-Oxa-17-(p-fluorophenyl)-18,19,20-trinor-;
3-Oxa-16-methyl-17-phenyl-18,19,20-trinor-;
3-Oxa-16,16-dimethyl-17-phenyl-18,19,20-trinor-;
3-Oxa-16-fluoro-17-phenyl-18,19,20-trinor-;
3-Oxa-16,16-difluoro-17-phenyl-18,19,20-trinor-;
3-Oxa-16-phenoxy-17,18,19,20-tetranor-;
3-Oxa-16-(m-trifluoromethylphenoxy)-17,18,19,20-tetranor-;
3-Oxa-16-(m-chlorophenoxy)-17,18,19,20-tetranor-;
3-Oxa-16-(p-fluorophenoxy)-17,18,19,20-tetranor-;
3-Oxa-16-phenoxy-18,19,20-trinor-;
3-Oxa-16-methyl-16-phenoxy-18,19,20-trinor-;
3-Oxa-13,14-didehydro-;
3-Oxa-16-methyl-13,14-didehydro-;
3-Oxa-16,16-dimethyl-13,14-didehydro-;
3-Oxa-16-fluoro-13,14-didehydro-;
3-Oxa-16,16-difluoro-13,14-didehydro-;
3-Oxa-17-phenyl-18,19,20-trinor-13,14-didehydro-;
3-Oxa-17-(m-trifluoromethylphenyl)-18,19,20-trinor-13,14-didehydro-;
3-Oxa-17-(m-chlorophenyl)-18,19,20-trinor-13,14-didehydro-;
3-Oxa-17-(p-fluorophenyl)-18,19,20-trinor-13,14-didehydro-;
3-Oxa-16-methyl-17-phenyl-18,19,20-trinor-13,14-didehydro-;
3-Oxa-16,16-dimethyl-17-phenyl-18,19,20-trinor-13,14-didehydro-;
3-Oxa-16-fluoro-17-phenyl-18,19,20-trinor-13,14-didehydro-;
3-Oxa-16,16-difluoro-17-phenyl-18,19,20-trinor-13,14-didehydro-;
3-Oxa-16-phenoxy-17,18,19,20-tetranor-13,14-didehydro-;
3-Oxa-16-(m-trifluoromethylphenoxy)-17,18,19,20-tetranor-13,14-didehydro-;
3-Oxa-16-(m-chlorophenoxy)-17,18,19,20-tetranor-13,14-didehydro-;
3-Oxa-16-phenoxy-18,19,20-trinor-13,14-didehydro-;
3-Oxa-16-methyl-16-phenoxy-18,19,20-trinor-13,14-didehydro-;
3-Oxa-13,14-dihydro-;
3-Oxa-16-methyl-13,14-dihydro-;
3-Oxa-16,16-dimethyl-13,14-dihydro-;
3-Oxa-16-fluoro-13,14-dihydro-;
3-Oxa-16,16-difluoro-13,14-dihydro-;
3-Oxa-17-phenyl-18,19,20-trinor-13,14-dihydro-;
3-Oxa-17-(m-trifluoromethylphenyl)-18,19,20-trinor-13,14-dihydro-;
3-Oxa-17-(m-chlorophenyl)-18,19,20-trinor-13,14-dihydro-;
3-Oxa-17-(p-fluorophenyl)-18,19,20-trinor-13,14-dihydro-;
3-Oxa-16-methyl-17-phenyl-18,19,20-trinor-13,14-dihydro-;
3-Oxa-16,16-Dimethyl-17-phenyl-18,19,20-trinor-13,14-dihydro-;
3-Oxa-16-fluoro-17-phenyl-18,19,20-trinor-13,14-dihydro-;
3-Oxa-16,16-difluoro-17-phenyl-18,19,20-trinor-13,14-dihydro-;
3-Oxa-16-phenoxy-17,18,19,20-tetranor-13,14-dihydro-;
3-Oxa-16-(m-trifluoromethylphenoxy)-17,18,19,20-tetranor-13,14-dihydro-;
3-Oxa-16-(m-chlorophenoxy)-17,18,19,20-tetranor-13,14-dihydro-;
3-Oxa-16-(p-fluorophenoxy)-17,18,19,20-tetranor-13,14-dihydro-;
3-Oxa-16-phenoxy-18,19,20-trinor-13,14-dihydro-;
3-Oxa-16-methyl-16-phenoxy-18,19,20-trinor-13,14-dihydro-;
3-Oxa-cis-13-;
3-Oxa-16-methyl-cis-13-;
3-Oxa-16,16-dimethyl-cis-13-;
3-Oxa-16-fluoro-cis-13-;
3-Oxa-16,16-difluoro-cis-13-;
3-Oxa-17-phenyl-18,19,20-trinor-cis-13-;
3-Oxa-17-(m-trifluoromethylphenyl)-18,19,20-trinor-cis-13-;
3-Oxa-17-(m-chlorophenyl)-18,19,20-trinor-cis-13-;
3-Oxa-17-(p-fluorophenyl)-18,19,20-trinor-cis-13-;
3-Oxa-16-methyl-17-phenyl-18,19,20-trinor-cis-13-;
3-Oxa-16,16-dimethyl-17-phenyl-18,19,20-trinor-cis-13-;
3-Oxa-16-fluoro-17-phenyl-18,19,20-trinor-cis-13-;
3-Oxa-16,16-difluoro-17-phenyl-18,19,20-trinor-cis-13-;
3-Oxa-16-phenoxy-17,18,19,20-tetranor-cis-13-;
3-Oxa-16-(m-trifluoromethylphenoxy)-17,18,19,20-tetranor-cis-13-;
3-Oxa-16-(m-chlorophenoxy)-17,18,19,20-tetranor-cis-13-;
3-Oxa-(p-fluorophenoxy)-17,18,19,20-tetranor-cis-13-;
3-Oxa-16-phenoxy-18,19,20-trinor-cis-13-;
3-Oxa-16-methyl-16-phenoxy-18,19,20-trinor-cis-13-;
3-Oxa-13,14-dihydro-trans-14,15,-didehydro-;
3-Oxa-16-methyl-13,14-dihydro-trans-14,15-didehydro-;
3-Oxa-16,16-dimethyl-13,14-dihydro-trans-14,15-didehydro-;
3-Oxa-16-fluoro-13,14-dihydro-trans-14,15-didehydro-;
3-Oxa-16,16-difluoro-13,14-dihydro-trans-14,15-didehydro-;

3-Oxa-17-phenyl-18,19,20-trinor-13,14-dihydro-trans-14,15-didehydro-;
3-Oxa-17-(m-trifluoromethylphenyl)-18,19,20-trinor-13,14-dihydro-trans-14,15-didehydro-;
3-Oxa-17-(m-chlorophenyl)-18,19,20-trinor-13,14-dihydro-trans-14,15-didehydro-;
3-Oxa-17-(p-fluorophenyl)-18,19,20-trinor-13,14-dihydro-trans-14,15-didehydro-;
3-Oxa-16-methyl-17-phenyl-18,19,20-trinor-13,14-dihydro-trans-14,15-didehydro-;
3-Oxa-16,16-Dimethyl-17-phenyl-18,19,20-trinor-13,14-dihydro-trans-14,15-didehydro-;
3-Oxa-16-fluoro-17-phenyl-18,19,20-trinor-13,14-dihydro-trans-14,15-didehydro-;
3-Oxa-16,16-difluoro-17-phenyl-18,19,20-trinor-13,14-dihydro-trans-14,15-didehydro-;
3-Oxa-16-phenoxy-17,18,19,20-tetranor-13,14-dihydro-trans-14,15-didehydro-;
3-Oxa-16-(m-trifluoromethylphenoxy)-17,18,19,20-tetranor-13,14-dihydro-trans-14,15-didehydro-;
3-Oxa-16-(m-chlorophenoxy)-17,18,19,20-tetranor-13,14-dihydro-trans-14,15-didehydro-;
3-Oxa-16-(p-fluorophenoxy)-17,18,19,20-tetranor-13,14-dihydro-trans-14,15-didehydro-;
3-Oxa-16-phenoxy-18,19,20-trinor-13,14-dihydro-trans-14,15-didehydro-; and
3-Oxa-16-methyl-16-phenoxy-18,19,20-trinor-13,14-dihydro-trans-14,15-didehydro-.

Likewise following the procedures of Preparations 1, 2, and 3 as described above, but employing corresponding starting materials, there are prepared the formula-VII 9-deoxy-6,9-epoxy-5-iodo-PGF$_{1\alpha}$-type compounds, formula-III 6-keto-PGF$_{1\alpha}$-type compounds, and formula-XX 9-deoxy-6,9-epoxy-6-hydroxy-PGF$_{1\alpha}$-type compounds having the following structural features:
2,3-Didehydro-;
2,2-Dimethyl-;
2a,2b-Dihomo-;
4-Oxa-4a-homo-;
7a-Homo-;
11$\beta$-;
11-Deoxy-;
11-Deoxy-11-methylene-;
11-Deoxy-11-hydroxymethyl-;
15$\beta$-;
15-Keto-;
15-Deoxy-;
15-Methyl-15(S)-;
15-Methyl-15(R)-; and
17,18-Didehydro-.

Preparation 4

5$\xi$-Iodo-9-deoxy-6,9-epoxy-PGF$_{1\alpha}$, p-Phenylphenacyl Ester (Formula VII).

A mixture of the formula-VII iodo acid compound (Preparation 3, Formula VII, 0.20 g.), p-phenylphenacyl bromide (0.50 g.), 0.4 ml. of diisopropylethylamine, and 10 ml. of acetonitrile is stirred at about 25° C. for 40 min. It is mixed with dilute aqueous citric acid and brine and extracted with ethyl acetate. The organic phase is dried and concentrated. The residue is subjected to silica gel chromatography, eluting with ethyl acetate (25-100%)-Skellysolve B to yield the title 5-iodo compound as a colorless oil, 0.20 g.

Preparation 5

2-Decarboxy-2-azidomethyl-PGF$_{2\alpha}$, or 2-nor-PGF$_{2\alpha}$, azide (Formula CV: Z$_1$ is —CH=CH—(CH$_2$)$_3$— or —CH=CH—(CH$_2$)$_2$—, respectively, R$_{31}$ is hydroxy, Y$_1$ is trans —CH=CH—, R$_{34}$ and R$_{35}$ of the L$_1$ moiety and R$_{33}$ of the M$_1$ moiety are all hydrogen, and R$_{30}$ is n-butyl).

A. To a cold solution (0° C.) of PGF$_{2\alpha}$ (7.1 g.), 125 ml. of acetone, 10 ml. of water, and 2.2 g. of triethylamine is added with stirring 3.01 g. of isobutylchloroformate. The mixture is stirred at 0° C. for about 30 min. at which time a cold solution of 7 g. of sodium azide on 35 ml. of water is added. The mixture is then stirred at 0° C. for one hr. at which time it is diluted with 300 ml. of water and extracted with diethyl ether. The organic layers are then combined; washed with water, dilute carbonate solution, saturated saline; dried; and concentrated under reduced pressure, maintaining bath temperature below 30° C., to yield 2-nor-PGF$_{2\alpha}$, azide.

B. 2-Decarboxy-2-azidomethyl-PGF$_{2\alpha}$ is prepared by the following reaction sequence:

(1) A solution of t-butyldimethylsilyl chloride (10 g.), imidazole (9.14 g.), and PGF$_{2\alpha}$ (3 g.) in 12 ml. of dimethylformamide are magnetically stirred under nitrogen atmosphere for 24 hr. The resulting mixture is then cooled in an ice bath and the reaction quenched by addition of ice water. The resulting mixture is then diluted with 150 ml. of water and extracted with diethyl ether. The combined ethereal extracts are then washed with water, saturated ammonium chloride, a sodium chloride solution, and thereafter dried over sodium sulfate. Solvent is removed under vacuum yielding PGF$_{2\alpha}$, t-butyldimethylsilyl ester, 9,11,15-tris-(t-butyldimethylsilyl ether). NMR absorptions are observed at 0.20, 0.30, 0.83, 0.87, 0.89, 1.07–2.50, 3.10–4.21, and 5.38 $\delta$. Characteristic infrared absorptions are observed at 970, 1000, 1060, 1250, 1355, 1460, 1720, and 2950 cm$^{-1}$.

(2) To a magnetically stirred suspension of lithium aluminum hydride (7.75 g.) in 18 ml. of diethyl ether is added dropwise at room temperature over a period of 12 min. 8.71 g. of the reaction product of part (1) above in 40 ml. of diethyl ether. After stirring at ambient temperature for one hr., the resulting product is cooled in an ice water bath and saturated sodium sulfate is added dropwise until the appearance of a milky suspension. The resulting product is coagulated with sodium sulfate, triturated with diethyl ether, and the solvent is removed by suction filtration. Concentration of the diethyl ether under vacuum yields 7.014 g. of 2-decarboxy-2-hydroxymethyl-PGF$_{2\alpha}$, 9,11,15-tris-(t-butyldimethylsilyl ether), NMR absorptions are observed at 0.03, 0.82, 0.87, 1.10–2.60, 3.30–4.30, and 5.37 $\delta$. Characteristic infrared absorptions are observed at 775, 840, 970, 1065, 1250, 1460, 2895, 2995, and 3350 cm$^{-1}$.

(3) p-Toluenesulfonyl chloride (3.514 g.), pyridine (44 ml.), and the reaction product of subpart (2), 7.014 g., are placed in a freezer at $-20°$ C. for 3 days. Thereafter, 7.200 g. of 2-decarboxy-2-p-toluenesulfonyloxymethyl-PGF$_{2\alpha}$, 9,11,15-tris-(t-butyldimethylsilyl ether), is recovered. NMR absorptions are observed at 0.10, 0.94, 0.97, 1.10, 2.50, 4.03, 3.80–4.80, 5.45, 7.35, and 7.80 $\delta$. Infrared absorptions are observed at 775, 970, 1180, 1190, 1250, 1360, 1470, 2900, and 2995 cm$^{-1}$.

(4) The reaction product of subpart (3) (2.13 g.) is placed in 42 ml. of acetic acid, tetrahydrofuran, and water (3:1:1) containing 0.25 ml. of 10 percent aqueous hydrochloric acid. The reaction mixture becomes homogeneous after vigorous stirring for 16 hr. at room temperature. The resulting solution is then diluted with 500 ml. of ethyl acetate; washed with saturated sodium chloride and ethyl acetate; dried over sodium sulfate; and evaporated under reduced pressure, yielding 1.301 g. of an oil. Crude product is chromatographed on 150 g. of silica gel packed with ethyl acetate. Eluting with ethyl acetate yields 0.953 g. of 2-decarboxy-2-p-toluenesulfonyloxymethyl-PGF$_{2\alpha}$.

(5) The reaction product of subpart (4), (0.500 g.) in 5.0 ml. of dimethylformamide was added to a stirred suspension of sodium azide (1.5 g.) in 20 ml. of dimethylformamide. Stirring is continued at ambient temperature for 3 hr. The reaction mixture is then diluted with water (75 ml.), extracted with diethyl ether (500 ml.), and the etheral extracts washed successively with water, saturated sodium chloride, and dried over sodium sulfate. Removal of the diethyl ether under reduced pressure yields 0.364 g. of 2-decarboxy-2-azidomethyl-PGF$_{2\alpha}$. A characteristic azido infrared absorption is observed at 2110 cm$^{-1}$.

Preparation 6

2-Decarboxy-2-aminomethyl-PGF$_{2\alpha}$ (Formula CXXV: Z$_1$ cis—CH=CH—(CH$_2$)$_3$—, R$_{31}$ is hydroxy, Y$_1$ is trans—CH=CH—, R$_{34}$ and R$_{35}$ of the L$_1$ moiety and R$_{33}$ of the M$_1$ moiety are all hydrogen, and R$_{30}$ is n-butyl).

Crude 2-decarboxy-2-azidomethyl-PGF$_{2\alpha}$ (Prep. 5, 0.364 g.) in 12 ml. of diethyl ether is added to a magnetically stirred suspension of lithium aluminum hydride (0.380 g.) in 20 ml. of diethyl ether. Reaction temperature is maintained at about 0° C. and addition of lithium aluminum hydride proceeds dropwise over a 4 min. period. After addition is complete, the resulting mixture is stirred at ambient temperature for 1.5 hr. and thereafter placed in an ice bath (0°-5° C.). Excess reducing agent is then destroyed by addition of saturated sodium sulfate. After cessation of gas evolution, the resulting product is coagulated with sodium sulfate, triturated with diethyl ether, and solid salts removed by filtration. The filtrate is then dried with sodium sulfate, and evaporated under reduced pressure to yield 0.304 g. of a slightly yellow oil. This oil (100 mg.) is then purified by preparative thin layer chromatography, yielding 42 g. of title product. NMR absorptions are observed at 0.90, 1.10–2.80, 3.28, 3.65–4.25, and 5.45 δ. Characteristic infrared absorptions are observed at 970, 1060, 1460, 2995, and 3400 cm$^{-1}$. The mass spectrum shows parent peak at 699.4786 and other peaks at 628, 684, 595, 217, and 274.

Preparation 7

5ξ-Iodo-9-deoxy-6ξ,9α-epoxy-PGF$_1$, Amide, less polar and more polar isomers (Formula VII: D is —(CH$_2$)$_3$—, Q is

R$_4$ is n-pentyl,

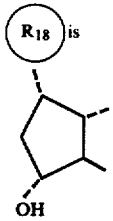

R$_{19}$ is

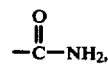

R$_{37}$ is iodo and X is trans—CH=CH—).

A solution of the formula-VII iodo-ether acid, mixed isomers (Preparation 3, 5.0 g.) in 50 ml. of acetone is cooled to about −10° C. and treated with 3.0 ml. of triethylamine and 3.0 ml. of isobutyl chloroformate. After 5 min. there is added 100 ml. of acetonitrile saturated with ammonia, and the reaction mixture allowed to warm to about 25° C. The mixture is filtered, and the filtrate concentrated. The residue is taken up in ethyl acetate and water. The organic phase is washed with water, dried over magnesium sulfate and concentrated. The residue is subjected to silica gel chromatography, eluting with acetone (25–100%)-methylene chloride. There are obtained the formula-VII iodo-ether, amide, less polar isomer, 0.02 g., having R$_f$0.40 (TLC on silica gel in acetone); a fraction of mixed less and more polar isomers, 2.2 g.; and the more polar isomer, 1.5 g., having R$_f$0.37 (TLC on silica gel in acetone), infrared absorption at 3250, 3150, 1660, 1610, 1085, 1065, 1050, and 965 cm$^{-1}$, and NMR peaks at 6.4, 5.5, 3.5–4.7 and 0.9 δ.

Preparation 8

5ξ-Iodo-9-deoxy-6ξ,9α-epoxy-PGF$_1$, Methylamide, mixed isomers (Formula VII: R$_{19}$ is

A solution of the formula-VII 5ξ-iodo-9-deoxy-6ξ,9α-epoxy-PGF$_1$, mixed isomers (Preparation 3, 4.66 g.) in 50 ml. of acetone is treated with 1.42 ml. of triethylamine and cooled to −5° C. Thereupon 1.3 ml. of isobutyl chloroformate is added, with stirring at 0° C. for 5 min., followed by 25 ml. of 3 M methylamine in acetonitrile. The solution is stirred for 20 min. more as it warmed to about 25° C. The mixture is filtered and concentrated. The oily residue is triturated with methylene chloride, and filtered to remove a precipitate. The filtrate is subjected to silica gel chromatography, eluting with acetone (50–90%)-methylene chloride, to yield the 5ξ-iodo-9-deoxy-6ξ,9α-epoxy-PGF$_1$, methylamide mixed isomers, 3.45 g., having NMR peaks at 6.3, 5.4–5.7, 3.2–4.7, 2.78, and 0.7–2.65 δ.

Preparation 9

5ξ-Iodo-9-deoxy-6ξ,9α-epoxy-PGF$_1$, n-Butylamide, Mixed Isomers (Formula: VII: R$_{19}$ is

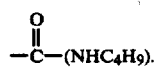

A solution of the formula-VII iodo-ether acid, mixed isomers (Preparation 3, 5.0 g.) in 50 ml. of acetone is cooled to about −10° C. and treated with 2.0 ml. of triethylamine and 1.9 ml. of isobutyl chloroformate. After 6 min. there is added a solution of 15 ml. of n-butylamine in 20 ml. of acetone. After about 15 min. the reaction mixture is allowed to warm to about 25° C. and stirred for 3 hr. The mixture is concentrated and the residue is taken up in ethyl acetate. The solution is washed with water and brine, dried over magnesium sulfate, and concentrated. The residue is chromatographed on silica gel, eluting with acetone (5–100%)-methylene chloride to yield the title compounds, 5.3 g. The product is rechromatographed to remove color using silica gel and eluting with acetone-methylene chloride (1:3). From 0.48 g. there is obtained the title compounds as a pale yellow oil, 0.35 g., having $R_f$ 0.63 (TLC on silica gel in acetone), and infrared absorption peaks at 3300, 3100, 1735, 1715, 1645, 1555, 1070, 1055, 1020, and 965 cm$^{-1}$.

Preparation 10

6-Keto-PGF$_{1\alpha}$, n-Butylamide

I. There is first prepared (5Z)-9-deoxy-6,9α-epoxy-Δ$^5$-PFG$_1$, n-butylamide. A solution of 5ξ-iodo-6ξ,9α-epoxy-PGF$_1$ n-butylamide (Preparation 9, 3.5 g.) in 100 ml. of benzene is treated with 8 ml. of DBN at 40°–45° C. for about 16 hr. The mixture is cooled, diluted with ice water, and extracted with chloroform, keeping a few drops of triethylamine in the organic phase. The combined organic phases are washed with ice water, dried and concentrated to an oil, 3.64 g. Of this, 3.1 g. is taken up in warm diethyl ether, and the ether solution when cooled yields 1.5 g., mainly solid. The product is recrystallized from ether, 0.85 g., m.p. 102°–104° C.

II. A solution of the above (5Z)-9-deoxy-6,9α-epoxy-Δ$^5$-PGF$_2$, n-butylamide (3.0 g.) in 25 ml. of tetrahydrofuran is treated with sufficient 10% aqueous potassium hydrogen sulfate solution to bring the pH to 5.0. The mixture is concentrated to remove tetrahydrofuran and the residue is taken up in water and ethyl acetate. Sodium chloride is added to saturation and the organic phase is separated. The aqueous phase is extracted with acetone-ethyl acetate (1:4) and the organic phases are combined. The organic phases are washed with brine, dried, and concentrated. The residue, 2.10 g., is chromatographed on silica gel, eluting with acetone (33–100%)-methylene chloride to yield a 1:1 mixture of the title compound together with the corresponding 9-deoxy-6,9α-epoxy-6-hydroxy compound, having $R_f$ 0.57 (TLC on silica gel in acetone). The mixture is dissolved in 10 ml. of tetrahydrofuran and acidified with aqueous potassium hydrogen sulfate, thereby converting the mixture to substantially all 6-keto-PGF$_{1\alpha}$, n-butylamide, having $R_f$ 0.58 (TLC on silica gel in acetone). The product is recovered by concentrating the solution, portioning between ethyl acetate and water, washing the organic phase with brine, and concentrating to an oil, 1.90 g., having a high resolution mass spectral peak (TMS derivative) at 641.4258.

Preparation 11

5ξ-Iodo-9-deoxy-6ξ,9α-epoxy-PGF$_1$, Benzylamide, mixed isomers (Formula VII: R$_{19}$ is

Following the procedures of Preparation 8, there are used 4.66 g. of the formula-VII 5ξ-iodo-9-deoxy-6ξ,9α-epoxy-PGF$_1$, mixed isomers, and 1.08 g. of benzylamine instead of methylamine. The crude product is chromatographed on silica gel, eluting with acetone (50–70%)-methylene chloride, to yield the 5ξ-iodo-9-deoxy-6ξ-9α-epoxy-PGF$_1$, benzylamide mixed isomers, 4.1 g., having NMR peaks at 7.3, 6.6, 5.3–5.7, and 3.5–4.6 δ.

Preparation 12

5ξ-Iodo-9-deoxy-6ξ,9α-epoxy-PGF$_1$, Anilide, mixed isomers (Formula VII R$_{19}$ is

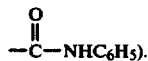

Following the procedures of Preparation 8, there are used 4.66 g. of the formula-VII 5ξ-iodo-9-deoxy-6ξ,9α-epoxy-PGF$_1$, mixed isomers, and 0.94 g. of aniline. The crude product is chromatographed on silica gel, eluting with acetone (10–50%)-methylene chloride, to yield the 5ξ-iodo-9-deoxy-6ξ,9α-epoxy-PGF$_1$, anilide mixed isomers, 4.0 g., having NMR peaks at 8.4, 6.9–7.7, 5.3–5.7, and 3.4–4.7 δ.

EXAMPLE 1

6-Keto-PGE$_1$, Methyl Ester (Formula VI: D is —(CH$_2$)$_3$—, Q is

R$_4$ is n-pentyl,

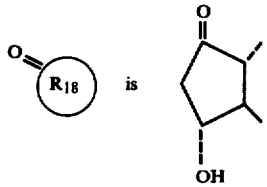

R$_{19}$ is —COOCH$_3$, and X is trans—CH=CH—).

A. Refer to Chart A. A solution of formula-III 6-Keto-PGF$_{1\alpha}$, methyl ester (0.50 g.) in 25 ml. of methylene chloride is treated with 3 ml. of dihydropyran and 3 ml. of a saturated solution of pyridine hydrochloride in methylene chloride and left standing about 5 hr. at about 25° C. or until TLC shows that the starting material has disappeared. and that the bis(tetrahydropyranyl)ether has been formed, having $R_f$ 0.22 (TLC on silica gel in acetone-methylene chloride (1:9)) or $R_f$ 0.47 (TLC on silica gel in acetone-methylene chloride (1:3)). The reaction mixture is concentrated, washed with aqueous sodium bicarbonate and brine, dried, and concentrated. The residue is subjected to silica gel chromatography, eluting with acetone (10–25%) in methylene chloride to yield the formula-IV bis(tetrahydropyranyl) ether, methyl ester, having infrared peaks at 3500, 1745, 1730, 1200, 1160, 1130, 1110, 1075, 1035, 1020, 980, 915, 870, 815, and 735 cm$^{-1}$; mass spectral lines (TMS) at 552, 522, 366, 348, 331, 330, 304, and 85; and NMR spectral peaks at 5.5, 4.67, 3.65, 3.2–3.7, and 0.9 δ.

B. The reaction product from part A, containing 6-keto-PGF$_{1\alpha}$, bis(tetrahyropyranyl)ether, methyl ester corresponding to formula IV, is oxidized to compound V. A composite from several lots, weighing 0.93 g., in 20 ml. of acetone is treated at $-10°$ C. with 2.0 ml. of Jones reagent. After stirring for 1.5 hr. the reaction mixture is quenched with isopropanol and extracted with diethyl ether. The extract is washed with brine, dried, and concentrated. The residue is subjected to silica gel chromatography, eluting with ethyl acetate (20–50%)-Skellysolve B to yield the formula-V 6-keto-PGE$_1$, bis(tetrahydropyranyl)ether, methyl ester, 0.52 g., having R$_f$0.52 (TLC on silica gel in ethyl acetate-Skellysolve B (1:1)); and infrared peaks at 1745 and 1725 cm$^{-1}$ (free of OH at 3000–3500).

C. The product of part B is hydrolyzed in 3 ml. of acetic acid and 1.5 ml. of water at 40° C. for 3 hr., then mixed with brine and extracted with chloroform. The organic phase is washed with brine, dried, and concentrated. The residue is subjected to silica gel chromatography eluting with ethyl acetate (25–100%) -Skellysolve B to yield 0.15 g. of the title compound, having infrared peaks at 3380, 1750, 1710, 1250, 1200, 1180, 1105, 1070, and 975 cm$^{-1}$, and mass spectral lines (TMS) at 526.3123, 511, 508, 495, 455, 436, 382, 313.2004, and 199. An analytical sample, recrystallized as needles from diethyl ether-hexane, m. 39°–40° C., has R$_f$0.33 (TLC on silica gel in ethyl acetate).

EXAMPLE 2

6-Keto-PGE$_1$ (Formula VI: D is —(CH$_2$)$_3$—, Q is

R$_4$ is n-pentyl,

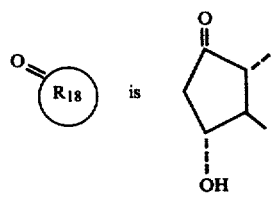

R$_{19}$ is —COOH, and X is trans—CH=CH—).

A. Refer to Chart B. There is first prepared the formula-VIII bis(tetrahydropyranyl)ether of 9-deoxy-6,9-epoxy-5-iodo-PGF$_{1\alpha}$, methyl ester. The formula-VII product of Preparation 1 (2.0 g.) in 20 ml. of methylene chloride, together with 4 ml. of dihydropyran and 1 ml. of a saturated solution of pyridine hydrochloride in methylene chloride, is left standing 16 hr. at about 25° C. The mixture is washed with aqueous sodium bicarbonate and brine, dried and concentrated to a colorless oil. The residue is subjected to silica gel chromatography, eluting with acetone (10%)-methylene dichloride, to yield about 3.0 g. having R$_f$0.73 (TLC on silica gel in ethyl acetate); and infrared peaks at 1765, 1215, 1140, 1085, 1045, 1036, 985, 875, 820, and 740 cm$^{-1}$ (free of OH at 3000–3500).

B. The formula-IV 6-keto PGF-type compound is prepared in several steps as follows. The product of part A above (about 3.0 g.) is mixed with 100 ml. of benzene and 4 ml. of 1,5-diazabicyclo[4.3.0]nonene-5 (DBN) and held at 40° C. for 4 hr., then at about 25° C. for 64 hr. The mixture is washed with ice-water, dried over magnesium sulfate, and concentrated to the enol ether, 9-deoxy-6,9-epoxy-Δ$^5$-PGF$_{1\alpha}$, bis(tetrahydropyranyl)ether, methyl ester, 2.5 g. having NMR peaks at 5.55, 4.5–5.1, 3.2–4.5, and 0.9 δ; and infrared peaks at 1740, 1695, 1200, 1165, 1130, 1075, 1035, 1020, 975, and 870 cm$^{-1}$.

The enol ether (2.25 g.) is dissolved in 25 ml. of diethyl ether, mixed with 10 ml. of a dilute aqueous solution of potassium hydrogen sulfate and stirred at about 25° C. The reaction is monitored by TLC (silica gel plates in acetone (10%)-methylene chloride) as a more polar material is slowly formed. After several hours 50 ml. of tetrahydrofuran is added and stirring continued. The mixture is concentrated and the residue is extracted with ethyl acetate. The extract is washed with brine, dried, and concentrated to an oil. The residue is subjected to silica gel chromatography eluting with acetone (10–25%)-methylene chloride to yield the formula-IV 6-keto-PGF$_{1\alpha}$, bis(tetrahydropyranyl)ether, methyl ester, 1.91 g., having R$_f$0.22 (TLC on silica gel in acetone (10%)-methylene chloride), having the same infrared spectrum as the corresponding formula-IV intermediate of Example 1.

C. The acid form of the product of part B is prepared by saponifying that product. The methyl ester of part B (0.75 g.) in 25 ml. methanol and 7 ml. of 3 N. sodium hydroxide is stirred at about 25° C. for 3 hr. The mixture is chilled, saturated with sodium chloride, acidified with potassium hydrogen sulfate, and extracted with ethyl acetate. The extract is washed with brine, dried, and concentrated to an oil, 0.68 g., having R$_f$0.61 (TLC on silica gel in A-IX solvent).

D. The formula-V 6-keto PGE-type compound is obtained as follows. The product of part C (0.68 g.) in 50 ml. of acetone is cooled to $-15°$ C. and treated with 2 ml. of Jones reagent added slowly with stirring. Stirring is continued at about the same temperature for one hr., then at $-5°$ C. for 0.5 hr. The reaction is quenched with isopropanol and the mixture concentrated to about half volume. Brine is added and the mixture extracted with diethyl ether. The extract is washed with brine, dried, and concentrated to a yellow oil, 0.61 g., having R$_f$ 0.64 (TLC on silica gel in A-IX). After silica gel chromatography a fraction is obtained, 0.31 g.

E. The formula-VI title compound is finally obtained on hydrolysis of the blocking groups. The product of part D (0.31 g.) is treated in 7 ml. of acetic acid and 3 ml. of water at 40° C. for one hr. and a further 16 hr. at about 25° C. Brine is added and the mixture is extracted with chloroform. The extract is washed with water, dried, and concentrated to an oil, 0.25 g. This product is subjected to silica gel chromatography, eluting with ethyl acetate (25–100%)-hexane to obtain the title compound, 0.065 g. having NMR peaks at 5.72, 5.57, 3.8–4.3, 2.1–2.8, and 0.9 δ; and infrared absorption peaks at 3420, 3000, 2800, 1755, 1740, 1710, 1315, 1255, 1190, 1160, 1110, 1065, and 970. An analytical sample is obtained as needles on recyrstallizing from diethyl ether-hexane, m. 67°–69° C.

Following the procedures of Example 2, but replacing the preparation of the formula-IV 6-keto PGF-type compound in part B with a preparation using silver carbonate and perchloric acid, the same end product is obtained. Thus, instead of part B, the product of part A (2.5 g.) is mixed with 80 ml. of tetrahydrofuran, silver carbonate (one gram) and 7 drops of 70% perchloric acid. The mixture is stirred vigorously at about 25° C. for 22 hr. Additional perchloric acid (3 drops) is added and stirring continued for 4 hr. The mixture is filtered, the filtrate treated wth brine and sodium carbonate, and extracted with ethyl acetate. The extract is washed with brine, dried, and concentrated to an oil, 2.6 g. Silica gel chromatography, eluting with acetone (10–40%)-methylene chloride, yields the formula-IV 6-keto-PGF$_{1\alpha}$, bis(tetrahydropyranyl)ether, methyl ester, an oil, 0.52 g. having R$_f$ 0.35 (TLC on silica gel in ethyl acetate-cyclohexane (1:1)). Thereafter the 6-keto-PGE$_1$ product is obtained following parts C, D, and E above.

Following the procedures of Example 1 and 2 and Chart B but replacing the formula-VII starting material with the appropriate formula-VII compounds obtained following Preparations 1, 2, and 3, there are obtained formula-VI compounds as follows:

2,2-Difluoro-6-keto-PGE$_1$, Methyl Ester
(15S)-15-Methyl-6-keto-PGE$_1$
(15R)-15-Methyl-6-keto-PGE$_1$
16,16-Dimethyl-6-keto-PGE$_1$
2,2-Difluoro-16,16-dimethyl-6-keto-PGE$_1$, methyl ester
2,2-Difluoro-(15S)-15-methyl-6-keto-PGE$_1$, methyl ester
16-Phenoxy-17,18,19,20-tetranor-6-keto-PGE$_1$
16-Phenyl-17,18,19,20-tetranor-6-keto-PGE$_1$
17-Phenyl-18,19,20-trinor-6-keto-PGE$_1$
2,2-Difluoro-16-phenoxy-17,18,19,20-tetranor-6-keto-PGE$_1$, methyl ester
13,14-Dihydro-6-keto-PGE$_1$
2,2-Difluoro-13,14-dihydro-6-keto-PGE$_1$, methyl ester
2,2-Difluoro-13,14-didehydro-6-keto-PGE$_1$, methyl ester.

EXAMPLE 3

6-Keto-13,14-didehydro-PGF$_{1\alpha}$, 11,15-bis(tetrahydropyranyl)ether (Formula XVIII: D$_1$ is —(CH$_2$)$_3$—, Q$_3$ is

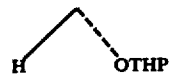

wherein THP is tetrahydropyranyl, R$_{23}$ is —COOH, R$_{26}$ is n-pentyl,

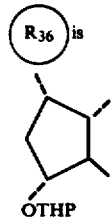

and X is —C≡C—) and 5ξ-Bromo-9-deoxy-6ξ,9-epoxy-14-bromo-15-keto-PGF$_{1\alpha}$, Methyl Ester.

A. Refer to Chart C. The 5ξ,6ξ,14-tribromo-15-keto-PFG$_{1\alpha}$, methyl ester (XII) is first prepared. A solution of 15-oxo-PGF$_{2\alpha}$, methyl ester (U.S. Pat. No. 3,728,382, 3.38 g.) in about 25 ml. of pyridine is treated dropwise with a soluton of pyridinium hydrobromide perbromide (7.08 g.) in 35 ml. of pyridine over 2.25 hr. Thereafter the mixture is stirred for 27 hr., diluted with ether and filtered. The filtrate is washed with water, cold hydrobromic acid (5%) aqueous sodium bicarbonate (5%), then dried and concentrated to yield 3.72 g. product. Similarly an additional 1.06 g. is prepared and combined. The product is subjected to silica gel chromatography eluting with hexane-ethyl acetate (65:35) to yield XII, 2.83 g., having NMR peaks at 0.90, 1.1–2.58, 2.58–3.4, 3.4–3.88, 3.67, 3.88–4.61, 6.96, and 7.03 δ; infrared peaks at 3400, 1730, 1685, 1610, 1245, 1200, 1170, 1085, and 1050 cm$^{-1}$; and mass spectral peaks (TMS) at 746.0562, 636, 634, 632, 630, 555, 553, and 551.

There is also obtained, as a separate fraction from the chromatography of the reaction product, 5ξ-bromo-9-deoxy-6ξ,9-epoxy-14-bromo-15-keto-PGF$_{1\alpha}$, methyl ester, 0.93 g., having NMR peaks at 0.90, 1.10–3.03, 3.03–3.46, 3.65, 3.78–5.0, 6.91 and 7.00 δ; infrared peaks at 3480, 2880, 2810, 1735, 1690, 1615, 1245, 1200, 1175, 1150, and 1080 cm$^{-1}$; and mass spectral peaks (TMS) at 594.099, 515, and 478.

B. 5ξ,6ξ,14-Tribromo-PGF$_{1\alpha}$, methyl ester (XIII). A solution of XII (2.38 g.) in 20 ml. of methanol is added to a solution of sodium borohydride (1.28 g.) in 40 ml. of methanol at −35° C. The temperature is held at −25° C. for 1 hr. The mixture is diluted with diethyl ether and quenched with acetic acid. The solution is washed with saline solution (5%) and aqueous bicarbonate (5%) solutons, dried, and concentrated to a mixture of C-15 epimers (XIII). Separation is achieved by silica gel chromatography eluting with hexane-ethyl acetate (3:2 followed by 1:1) to yield, first, the 15R epimer (XIII-15β), 1.57 g. having NMR peaks at 0.9, 1.1–3.35, 3.35–4.65, 3.66, and 5.75–6.21 δ; infrared peaks at 3380, 1735, 1725, 1250, 1200, 1175, 1075, and 1050 cm$^{-1}$; high resolution mass spectral peak (TMS derivative) at 749.0362, and [α]$_D$−11° in ethanol; and second, the 15S epimer (XIII-15α) 0.605 g. having NMR peaks at 0.9, 1.10–3.35, 3.35–4.6, 3.66, and 5.65–6.15 δ; infrared peaks at 3380, 1740, 1650, 1435, 1250, 1200, 1175, 1120, 1080, and 1045 cm$^{-1}$; high resolution mass spectral peak (TMS derivative) at 749.0384; and [α]$_D$−4° in ethanol.

C. 14-Bromo-PGF$_{2\alpha}$, methyl ester (XIV). A solution of XIII-15α (0.60 g.) in 20 ml. of methanol is treated with ammonium chloride (0.11 g.) and zinc dust (0.28 g.). The mixture is stirred for 1.5 hr., diluted with benzene and filtered. The filtrate is washed with 0.2 M. potassium acid sulfate, dried, and concentrated to yield 0.37 g., having R$_f$ 0.26 (TLC on silver nitrate-treated silica gel in ethyl acetate); NMR peaks at 0.88, 1.1–2.71, 2.71–3.55, 3.66, 3.80–4.35, 5.23–5.56 and 5.84 δ; and infrared peaks at 3320, 2900, 2820, 1940, 1650, 1430, 1310, 1240, 1215, 1170, 1115, and 1030 cm$^{-1}$.

D. 5ξ-iodo-9-deoxy-6ξ,9-epoxy-14-bromo-PGF$_{1\alpha}$, methyl ester (XV). A solution of XIV (1.9 g.) in 30 ml. of methylene chloride is added to a suspension of iodine (2.85 g.), potassium iodide (1.88 g.) sodium acetate (0.92 g.) and water (6 ml.). The mixture is stirred for 2 hr., treated with 20 ml. of 2 N. sodium thiosulfate, washed with aqueous 5% saline solution, dried and concentrated to yield XV, 2.95 g. An analytical sample obtained by subjecting a portion to silica gel chromatography had NMR peaks at 0.89, 1.1–3.18, 3.66, 3.6–4.8, and 5.88 δ; mass spectral peaks (TMS) at 701.1183, 645, 637, 589, 547, 529, 510, and 173; and infrared spectral peaks at 3380, 1740, 1655, 1230, 1170, 1080, and 1050 cm$^{-1}$.

E. 5ξ-iodo-9-deoxy-6ξ,9-epoxy-14-bromo-PGF$_{1\alpha}$, 11,15-bis(tetrahydropyranyl) ether, methyl ester (XVI). A solution of XV (1.0 g.) in 10 ml. of methylene chloride is treated with dihydropyran (3 ml.) and 3 ml. of a saturated solution of pyridine hydrochloride in methylene chloride. After 20 hr. the mixture is diluted with diethyl ether, washed with aqueous sodium bicarbonate (5%) and saline solution (5%), dried, and concentrated. The residue is 1.12 g., having NMR peaks at 0.9, 1.05–2.20, 2.2–3.2, 3.2–4.35, 3.66, 4.35–4.15, and 5.7–6.1 δ; and infrared peaks at 2900, 2820, 1760, 1440, 1350, 1210, 1125, 1090, 1035, 1025, 970, and 910 cm$^{-1}$.

F. 6-Keto-13,14-didehydro-PGF$_{1\alpha}$, 11,15-bis(tetrahydropyranyl)ether (XVII). A solution of XVI (1.1 g.) in 15 ml. of dimethyl sulfoxide and 1.5 ml. of methanol is treated with potassium t-butoxide (0.504 g.) for 20 hr. The mixture is diluted with 60 ml. of water, cooled, acidified with 5% phosphoric acid, and extracted wth diethyl ether. The organic phase is washed with brine, dried, and concentrated to an oil, 0.81 g., which is subjected to silica gel chromatography, eluting with hexane-ethyl acetate (7.5:2.5) to yield the title compound, 0.313 g., having NMR peaks at 0.9, 1.1–3.0, 3.05–5.1, and 6.5–7.5 δ; and infrared peaks at 3300, 3900, 2810, 2500–2700, 2225, 1740, 1710, 1430–1460, 1190, 1130, 1120, 1075, 1035, 1015, 975, and 905 cm$^{-1}$.

EXAMPLE 4

6-Keto-13,14-didehydro-PGE$_1$ (Formula VI: D is —(CH$_2$)$_3$—, Q is

R$_4$ is n-pentyl,

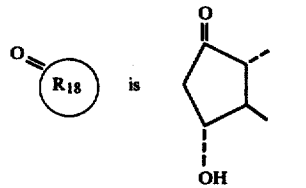

R$_{19}$ is —COOH, and X is —C≡C—).

Refer to Chart A. A solution of the formula-IV 6-keto-13,14-didehydro-PGF$_{1\alpha}$, 11,15-bis(tetrahydropyranyl)ether (Example 3, 1.1 g.) in 12 ml. of acetone is treated at −10° C. with 2.67 M. Jones reagent added dropwise in three 1 ml. aliquots at 15 min. intervals. The mixture is quenched with isopropanol added dropwise, diluted with diethyl ether, and partitioned with 5% aqueous sodium chloride, dried, and concentrated. The residue consists of the formula-V bis(tetrahydropyranyl)ether of the title compound, 0.26 g., having R$_f$0.29 (TLC on silica gel in A-IX-cyclohexane (1:1)).

The product above is hydrolyzed in a mixture of acetic acid (15 ml.), water (7.5 ml.) and tetrahydrofuran (1.0 ml.) for 4.5 hr. at about 40° C., then diluted with 30 ml. of water and lyophilized to a yellow oil, 0.14 g. The oil is subjected to silica gel chromatography, eluting with hexaneethyl acetate (3:2), to yield the title compound, 0.048 g., having NMR peaks at 0.90, 1.1–2.05, 2.05–3.33, 4.03–4.70, and 5.5–6.3 δ; mass spectral peaks (TLC) at 582.3210, 567, 511, 492, 477, 436, 421, 410, 402, 387, 291.1768, 173, and 111; and infrared peaks at 3350, 2870, 2500–2600, 2810, 2240, 1740, 1710, 1450, 1400, 1155, and 1080 cm$^{-1}$.

EXAMPLE 5

6-Keto-13,14-didehydro-PGF$_{1\alpha}$ (Formula III: D is —(CH$_2$)$_3$—, Q is

R$_4$ is n-pentyl,

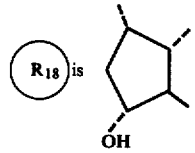

R$_{19}$ is —COOH, and X is —C≡C—).

A solution of the 5ξ-iodo-9-deoxy-6ξ,9-epoxy-14-bromo-PGF$_{1\alpha}$, methyl ester (Example 3D, 1.67 g.) in 30 ml. of dimethyl sulfoxide is treated with potassium tert-butoxide (1.63 g.) in 3 ml. of methanol at about 25° C. for 23 hr., then diluted with water (6 ml.) and reacted for a further 3 hr. The mixture is diluted with ether and partitioned with cold 3.5% phosphoric acid. The organic phase is washed with 5% sodium chloride solution, dried, and concentrated. The residue (0.87 g.) is subjected to silica gel chromatography eluting with hexane-ethyl acetate (1:1) to yield the formula-III title compound, 0.59 g., having NMR peaks at 0.90, 1.1–3.5, 3.7–5.2, and 5.28–6.51 δ; mass spectral peak (TMS derivative) at 670.3836; and infrared absorption peaks at 3360, 2670, 2230, 1710, 1320, 1245, 1205, 1145, 1115, 1090, 1055, and 995 cm$^{-1}$.

EXAMPLE 6

6-Keto-13,14-didehydro-PGF$_{1\alpha}$ and 6-Keto-13,14-didehydro-(15R)-PGF$_{1\alpha}$.

A. There are first prepared the 5ξ-bromo-9-deoxy-6ξ,9-epoxy (15R and 15S)-PGF$_{1\alpha}$ methyl ester compounds. A solution of the 5ξ-bromo-9-deoxy-6ξ,9-epoxy-14-bromo-15-keto-PGF$_{1\alpha}$, methyl ester (Example 3A, 0.93 g.) in 15 ml. of methanol is added to a solution of sodium borohydride (0.46 g.) in 50 ml. of methanol at −50° C. The reaction is continued at about −30° C. for 1.5 hr. The mixture is carefully acidified with 5 ml. of acetic acid in 250 ml. of diethyl ether. The solution is washed with 0.2 M. potassium hydrogen sulfate, 5% sodium chloride, and 5% sodium bicarbonate, then dried and concentrated to yield the mixed C-15 epimers. The product is combined with 0.39 g. from another run and subjected to silica gel chromatography, eluting with hexane-ethyl acetate (7:3). The respective fractions containing the 15R and 15S products yield 0.34 g. of the 15R and 0.34 g. of the 15S intermediate. The 15R compound has NMR peaks at 0.90, 1.1–2.75, 2.75–3.30, 3.66, 3.78–4.8, 5.80 and 5.90 δ; and infrared peaks at 3350, 1740, 1650, 1430, 1365, 1240, 1190, 1070, and 1050 cm$^{-1}$. The 15S compound has NMR peaks at 0.89, 1.1–3.2, 3.2–4.8, 3.66, 5.78, and 5.83 δ; and infrared peaks at 3350, 1740, 1650, 1430, 1365, 1240, 1190, 1070, and 1050 cm$^{-1}$.

B. A solution of the 15-S product from part A above (0.29 g.) in 5 ml. of dimethyl sulfoxide and 0.5 ml. of methanol is treated with potassium tert-butoxide (0.3 g.) for 20 hr. On hydrolysis of the methyl ester with 2 L N. NaOH for 3 hr. followed by dilution with 5% sodium chloride, acidifying with 10% phosphoric acid, extraction with diethyl ether, washing with 5% sodium chloride, drying, and concentrating there is obtained 0.20 g. residue. The residue is subjected to silica gel chromatography, eluting with hexane-ethyl acetate (1:1 to 3:2), to yield the 15S title compound, 0.065 g., having the same properties as the product of Example 5.

Likewise, using the 15R intermediate of part A there is obtained the corresponding 15R title compound having $R_f$ 0.20 (TLC on silica gel plates in A-IX solvent).

Following the procedures of Example 6 Part B but substituting sodium methoxide for potassium tert-butoxide there are also obtained the title compounds.

EXAMPLE 7

6-Keto-13,14-didehydro-(15R)-PGE$_1$ (Formula VI)

A. Refer to Chart C. There is first prepared the formula-XIV 14-bromo-(15R)-PGF$_{2\alpha}$, methyl ester. Following the procedure of Example 3-C above, the formula-XIII-15$\beta$ compound, (15R)-5$\xi$,6$\xi$,14-tribromo-PGF$_{1\alpha}$, methyl ester (1.52 g.) is treated with zinc dust and ammonium chloride in methanol to yield the formula-XIV 15R compound, 1.13 g., having $R_f$ 0.40 (TLC on silver nitrate-treated silica gel in ethyl acetate), NMR and infrared spectra very similar to those of the 15S epimer of Example 3-C.

B. 5$\xi$-iodo-9-deoxy-6$\xi$,9-epoxy-14-bromo-(15R)-PGF$_{1\alpha}$, methyl ester (XV). Following the procedure of Example 3-D, the formula-XIV 14-bromo-(15R)-PGF$_{2\alpha}$, methyl ester (0.98 g.) is iodinated to the formula-XV iodo compound. The product is chromatographed on silica gel, eluting with ethyl acetate (30%)-hexane to yield the desired compound, 0.88 g., having NMR and infrared spectra very similar to those of the 15S epimer of Example 3-D.

C. 5$\xi$-iodo-9-deoxy-6$\xi$,9-epoxy-14-bromo-(15R)-PGF$_{1\alpha}$, 11,15-bis(tetrahydropyran-2-yl ether), methyl ester (XVI). Following the procedure of Example 3-E, the formula-XV 5$\xi$-iodo-9-deoxy-6$\xi$,9-epoxy-14-bromo-(15R)-PGF$_{1\alpha}$, methyl ester (2.16 g.) is reacted with dihydropyran to form the formula-XVI bis (THP ether), 3.24 g., having $R_f$ 0.57 and 0.62 (TLC on silica gel in ethyl acetate-cyclohexane (1:2) and having NMR and infrared spectra very similar to those of the 15S epimer of Example 3-E.

D. 6-Keto-13,14-didehydro-(15R)-PGF$_{1\alpha}$, 11,15-bis(tetrahydropyran-2-yl ether) (XVII). Following the procedure of Example 3-F, the formula-XVI 5$\epsilon$-iodo-9-deoxy-6$\xi$,9-epoxy-14-bromo-(15R)-PGF$_{1\alpha}$, 11,15-bis(tetrahydropyran-2-yl ether), methyl ester (3.27 g.) is reacted with potassium t-butoxide in dimethyl sulfoxide-methanol, removing a less polar by-product by silica gel chromatography, to yield the product, 0.74 g., having $R_f$ 0.51 (TLC on silica gel in a solvent prepared by diluting the organic phase from ethyl acetate-acetic acid-cyclohexane-water (9:2:5:10) with half its volume of cyclohexane), and having NMR and infrared spectra very similar to those of the 15S epimer of Example 3-F.

E. 6-Keto-13,14-didehydro-(15R)-PGE$_1$, 11,15-bis(tetrahydropyran-2-yl ether) (V). Refer to Chart A. Following the procedure of Example 4, the formula-XVII (or IV) 6-keto-13,14-didehydro-(15R)-PGF$_{1\alpha}$, 11,15-bis(tetrahydropyran-2-yl ether) (0.46 g.) is oxidized with Jones reagent to the formula-V compound, 0.23 g., having $R_f$ 0.55 (TLC on silica gel in the solvent of section D above, having NMR peaks at 0.90, 1.1–3.2, 3.2–4.65, 4.65–5.2 and 8.91 δ, and infrared absorption bands at 2600–3200, 2220, 1740, 1710, 1195, 1120, 1070, 1035, 995, 980, 965, and 910 cm$^{-1}$.

F. 6-Keto-13,14-didehydro-(15R)-PGE$_1$ (VI). Following the procedure of Example 4, the above bis(THP ether) (0.23 g.) is hydrolyzed and chromatographed to yield the title compound, 0.10 g., m.p. 72° C. when crystallized from diethyl ether-methylene chloride-hexane, having $R_f$ 0.36 (TLC on silica gel in the organic phase from ethyl acetate-acetic acid-cyclohexane-water (9:2:5:10)), having NMR peaks at 0.90, 1.1–2.0, 2.0–3.2, 3.9–4.7, and 6.0–6.7 δ, and mass spectral peaks (TMS derivative) at 567.299, 564, 549, 511, 492, 477, 421, 402, 387, 367, 201, and 111.

EXAMPLE 8

2-Decarboxy-2-hydroxymethyl-6-keto-PGE$_1$, (Formula XXV: Q is

$R_2$ is hydrogen, $R_4$ is n-pentyl,

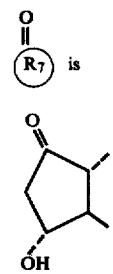

X is trans—CH=CH—, and f is one).

I. Refer to Chart E. There is first prepared the formula-XXIII 4,5-acetylenic PGF$_{1\alpha}$ type compound. The formula-XXII bis(THP ether) lactone (Corey et al., J. Am. Chem. Soc. 92, 397 (1970)) (6.5 g.) in 30 ml. of tetrahydrofuran is reacted with 4-trimethylsilyloxy-1-pentynyl-lithium (C.H. Lin, J. Org. Chem. 41, 4045 (1976) (3.6 g.) at −70° to −60° C. for about 0.5 hr. The adduct is isolated and dissolved in 30 ml. of isopropyl alcohol-water (4:1) and treated with about 0.5 ml. of 10% aqueous sodium hydrogen sulfate. The mixture is stirred at about 25° C. for 0.5 hr., treated with about 10 ml. of aqueous sodium bicarbonate, and concentrated to remove isopropyl alcohol. The residue is extracted with diethyl ether and the organic phase is washed with water, aqueous sodium hydrogen sulfate, aqueous sodium bicarbonate, and brine, dried, and concentrated. The residue is chromatographed on silica gel eluting with ethyl acetate-hexane (1:5), to yield the formula-XXIII 2-decarboxy-2-hydroxymethyl-4,4,5,5-tetradehydro-6-keto-PGF$_{1\alpha}$, 11,15-bis(tetrahydropyran-2-yl ether), 5.6 g. having NMR peaks at 5.68–5.36, 4.8–4.5, and 4.5–3.18 δ, infrared absorption peaks at 3440, 2210, 1675 and 975 cm$^{-1}$, and mass spectral lines (TMS derivative) at 649.3986, 563, 557, 509, 479, 478, 463, and 85.

II. There is next prepared the formula-XXIV 2-decarboxy-2-hydroxymethyl-4,4,5,5-tetradehydro-6-keto- PGE$_1$. The product of I above (2.6 g.) is treated in 50 ml. of acetone with Jones reagent (5.6 ml. of 2.67 M) in 30 ml. acetone added dropwise over 5 min. at −30° C. The reaction is quenched with aqueous sodium bisulfite and the mixture concentrated to remove acetone. The residue is extracted with ethyl acetate and the organic phase is washed with brine, dried, and concentrated. The resulting mixture is then methylated with diazomethane to form the methyl ester of any carboxylic acid present.

The above mixture containing 2-decarboxy-2-hydroxymethyl-4,5-tetradehydro-6-keto-PGE$_1$, 11,15-bis(tetrahydropyran-2-yl ether) and methyl ester byproducts is hydrolyzed in 20 ml. of acetic acid-tetrahydrofuran-water (3:1:1) at 40°–50° C. for 3 hr. The mixture is concentrated and the residue extracted with ethyl acetate. The organic phase is washed with aqueous sodium bicarbonate and brine, dried, and concentrated. The residue is chromatographed on silica gel (HPLC), eluting with acetone (25–50%)-hexane to obtain the more polar formula-XXIV compound, 0.278 g., having NMR peaks at 5.70–5.42, 4.32–3.80, and 3.23 δ, infrared absorption bands at 3480, 2210, 1755, 1670, and 970 cm$^{-1}$, and a high resolution mass spectral peak (TMS derivative) at 566.3299.

III. Finally, the title compound is obtained by catalytic hydrogenation of the above compound. The formula-XXIV compound of II above (0.35 g.), together with 35 mg. of palladium on barium sulfate and 5 ml. of pyridine is stirred under hydrogen at one atmosphere at about 25° C. for 0.5 hr. The solids are removed by filtration and the filtrate is concentrated. The residue is chromatographed on 30–50μ silica gel (HPLC), eluting with acetone-hexane (1:1) to yield the formula-XXV title compound, 0.178 g., having NMR peaks at 5.72–5.42, 4.34–3.78, and 3.60 δ, infrared absorption bands at 3360, 1745, 1710, 1590, 1160, 1070, 1015, and 970 cm$^{-1}$, and mass spectral lines (TMS derivative) at 570.3563, 555, 552, 499, 480, 465, 426, 409, 383, 375, 355, and 313.

Following the procedures of Example 8 and Chart E, but replacing the formula-XXII starting material with the appropriate lactone known in the art, there are obtained the following formula-XXV compounds 2-Decarboxy-2-hydroxymethyl-6-keto-16-phenyl-17,18,19,20-tetranor-PGE$_1$, 2-Decarboxy-2-hydroxymethyl-6-keto-(15S)-15-methyl-PGE$_1$, 2-Decarboxy-2-hydroxymethyl-6-keto-13,14-dihydro-PGE$_1$, 2-Decarboxy-2-hydroxymethyl-6-keto-13,14-didehydro-PGE$_1$.

Alternatively, the 13,14-dihydro- and 13,14-didehydro compounds are obtained by transformations of the above product of Example 8 or the formula-XXIV intermediate of Example 8 using methods known in the art.

EXAMPLE 9

6,15-Diketo-PGE$_1$ (Formula XXXV)

I. Refer to Chart F. The formula-XXX 11,15-bis(tetrahydropyran-2-yl ether) of 6-keto-PGF$_{1\alpha}$, methyl ester is first prepared. A solution of 6-keto-PGF$_{1\alpha}$, methyl ester (Johnson et al., J. Am. Chem. Soc. 99, 4182 (1977)) (0.3 g.) in 10 ml. of methylene chloride is treated with 2 ml. of dihydropyran and one ml. of a saturated solution of pyridine hydrochloride in methylene chloride and left standing at about 25° C. for several days. The mixture is washed with aqueous sodium bicarbonate, dried, and concentrated. The residue is chromatographed on silica gel, eluting with acetone (0–20%)-methylene chloride, to yield the bis(THP ether), 0.23 g., having R$_f$ 0.20 (TLC on silica gel in acetone (10%)-methylene chloride).

II. There is next prepared the formula-XXXII acid. The product above, combined with another lot of similar material (total 1.30 g.) is stirred with 40 ml. of methanol and 10 ml. of 3 N sodium hydroxide at about 25° C. for 3 hr. The mixture is cooled in an ice bath, saturated with sodium chloride, acidified with potassium hydrogen sulfate and immediately extracted with ethyl acetate. The organic phase is washed with brine, dried, and concentrated. The acid has R$_f$ 0.52 (TLC on silica gel in A-IX system).

III. There is next prepared the formula-XXXIV 15-oxo compound. The above product is immediately dissolved in 75 ml. of acetone, cooled to −15° C., and treated with 3 ml. of Jones reagent added slowly within 30 min. Stirring is continued for one hr., allowing the temperature to rise to −3° C.; then 0.5 ml. more Jones reagent is added, again at −10° C. and stirring continued for 45 min. The reaction is quenched with isopropyl alcohol, dried, and concentrated to an oil, about 1.5 g., having R$_f$ 0.7 (TLC on silica gel in A-IX system).

IV Finally, the title compound is obtained by hydrolysis. The above formula-XXXIV 6,15-diketo-PGE$_1$, 11,15-bis(tetrahydropyran-2-yl ether) is treated with 12 ml. of acetic acid and 5 ml. of water at 40° C. for 3 hrs. Then the mixture is cooled, diluted with brine, and extracted with chloroform. The organic phase is washed with brine, dried, and concentrated. The residue is chromatographed on 100 g. of silica gel, eluting with ethyl acetate (60–100%)-hexane, taking 50 ml. fractions and combining fractions 13–20, to yield the formula-XXXV title compound, 0.31 g., having R$_f$ 0.36 (TLC on silica gel in A-IX system), NMR peaks at 7.37, 6.82, 6.18, 4.2, 2.1–2.9, and 0.9 δ, and infrared absorption bands at 3400–3200, 2660, 1745, 1715, 1675, 1630, 1290, 1245, 1160, 1095, 1075, 975, 850, and 735 cm$^{-1}$.

EXAMPLE 10

6-Keto-PGE$_1$, Amide (Formula I)

A solution of 6-keto-PGE$_1$ (Example 2, 0.17 g.) in 7 ml. of acetone is treated at −10° C. with 0.2 ml. of triethylamine and 0.2 ml. of isobutylchloroformate. After 10 min. stirring the mixture is treated with 4 ml. of a saturated solution of ammonia in acetonitrile. After 15 min. at −10° C. the cooling bath is removed and stirring continued for 5 min. The mixture is then concentrated to one-half volume and diluted with water and ethyl acetate. The organic phase is separated, washed with brine, dried, and concentrated. The oily residue is chromatographed on silica gel, eluting with acetone (40–100%)-methylene chloride to yield the title compound, 0.075 g. An analytical sample is obtained by crystallizing from ethyl acetate-diethyl ether, a powder, m.p. 84°–6° C., having R$_f$ 0.23 (TLC on silica gel in methanol-acetic acid-chloroform (10:10:80)) and infrared absorption bands at 3540, 3420, 3200, 1745, 1710, 1655, 1620, 1295, 1245, 1160, 1110, 1075, 1025, and 975 cm$^{-1}$.

Following the procedures of Example 10, but replacing the starting material with (15S)-15-methyl-6-keto-PGE$_1$, there is obtained the formula-I compound: (15S)-15-Methyl-6-keto-PGE$_1$, amide.

EXAMPLE 11

6-Keto-PGE$_1$, Methylamide (Formula XL).

I. Refer to Chart G. There is first prepared the formula-XXXVII 11,15-bis(tetrahydropyran-2-yl ether). A mixture of the formula-VII 5ξ-iodo-9-deoxy-6ξ,9α-epoxy-PGF$_1$, methylamide (Preparation 8, 1.2 g.) in 25 ml. methylene chloride, with 2 ml. of dihydropyran and 25 mg. of p-toluenesulfonic acid monohydrate is stirred at about 25° C. for one hr. The mixture is then diluted with 75 ml. of methylene chloride, washed with saturated aqueous sodium bicarbonate and brine, dried, and concentrated. The residue, an oil, is chromatographed on silica gel, eluting with acetone (5–40%)-methylene chloride to yield the bis(THP ether) of the 5-iodo compound, mixed isomers, an oil, 1.6 g., having R$_f$ 0.10 and 0.03 (TLC on silica gel in acetone (10%)-methylene chloride).

II. There is next prepared the formula-XXXVIII 6-keto-PGF$_{1\alpha}$, methylamide, 11,15-bis(tetrahydropyran-2-yl ether). A solution of the above formula-XXXVII compound in 60 ml. of tetrahydrofuran is treated with silver carbonate (0.75 g.) and about 0.3 ml of perchloric acid, with stirring at about 25° C. for 20 hr. The mixture is filtered, diluted with ethyl acetate, washed with brine, dried, and concentrated to an oil, 1.4 g. The residue is chromatographed on silica gel, eluting with acetone (10–60%)-methylene chloride, to yield the formula-XXXVIII compound, 0.48 g., having R$_f$ 0.26 (TLC on silica gel in acetone-methylene chloride (1:1)).

III. Next is prepared the formula-XXXIX 6-keto-PGE$_1$, methylamide, 11,15-bis(tetrahydropyran-2-yl ether). A solution of the above formula-XXXVIII compound (0.48 g.) in 15 ml. of acetone is treated at −15° to −20° C. with one ml. of Jones reagent added dropwise and stirred for 45 min. Thereafter one ml. of isopropyl alcohol is added, with stirring for about 30 min. Brine and ethyl acetate are added and the organic phase is washed with brine, dried, and concentrated to an oil, 0.42 g., consisting of the title compound as its bis(THP ether).

IV. Finally, the above formula-XXXIX bis(THP ether) (0.42 g.) is treated in 9 ml. of acetic acid-water-tetrahydrofuran (20:10:3) at 40° C. for 3.5 hr. The solution is diluted with 15 ml. of water and freeze-dried. The residue is taken up in 10 ml. of methylene chloride and chromatographed over silica gel, eluting with acetone (30–80%)-methylene chloride to yield the title compound, 0.11 g., having R$_f$ 0.42 (TLC on silica gel in acetone), mass spectral lines (TMS derivative) at 597.3738, 582, 579, 507, 489, and 417, and infrared absorption bands at 3340, 1745, 1705, 1640, 1545, 1270, 1160, 1110, 1075, 1015, and 975 cm$^{-1}$.

EXAMPLE 12

6-Keto-PGE$_1$, n-Butylamide (Formula XL).

I. Refer to Chart G. There is first prepared the formula-XXXVIII 6-keto-PGF$_{1\alpha}$, n-butylamide, 11,15-bis-(tetrahydropyran-2-yl ether). A solution of 6-keto-PGF$_{1\alpha}$, n-butylamide (Preparation 10, 1.47 g.) in 50 ml. of chloroform is treated at about 25° C. with 8 ml. of dihydropyran and 5 ml. of methylene chloride saturated with pyridine hydrochloride. Additional amounts of reagents are added until the reaction is shown completed by TLC. The mixture is then washed with cold aqueous saturated sodium bicarbonate and brine, dried, and concentrated. The residue is chromatographed on silica gel, eluting with acetone-methylene chloride (1:2) to yield the formula-XXXVIII compound, 0.7 g., having R$_f$ 0.41 (TLC on silica gel in ethyl acetate).

II. Next is prepared the formula-XXXIX 6-keto-PGE$_1$, n-butylamide, 11,15-bis(tetrahydropyran-2-yl ether), using 0.7 g. of the above formula-XXXVIII compound and following the procedure of Example II–III, there is obtained 0.39 g. of product, having R$_f$ 0.55 (TLC on silica gel in ethyl acetate) and a strong infrared absorption band at 1740 cm$^{-1}$.

III. Finally, the title compound is obtained by hydrolyzing the product of II above (0.39 g.) in 2 ml. of glacial acetic acid and one ml. of water at 40° C. for 3 hr. The mixture is azeotroped with toluene, concentrating to a solid. The residue is chromatographed on silica gel, eluting with acetone-ethyl acetate (1:1) to yield the title compound, 0.2 g. An analytical sample is obtained on recrystallization from acetone-Skellysolve B, 0.15 g., having R$_f$ 0.20 (TLC on silica gel in ethyl acetate), and m.p. 78°–81° C.

EXAMPLE 13

6-Keto-PGE$_1$, Benzylamide (Formula XL).

I. Refer to Chart G. There is first prepared the formula-XXXVII 11,15-bis(tetrahydropyran-2-yl ether). Following the procedure of Example 8-I, the 5ξ-iodo-9-deoxy-6ξ,9α-epoxy-PGF$_1$, benzylamide (Preparation 11, 2.0 g.) is reacted with dihydropyran. The product, an oil, is chromatographed over silica gel, eluting with acetone (5–25%)-methylene chloride, to yield the bis(THP ether), 2.4 g., having R$_f$ 0.73 (TLC on silica gel in acetonemethylene chloride (1:1)).

II. There is next prepared the formula-XXXVIII 6-keto-PGF$_1$, benzylamide, 11,15-bis(tetrahydropyran-2-yl ether) using the above formula-XXXVII compound. There is first prepared (5Z)-9-deoxy-6,9α-epoxy-Δ$^5$-PGF$_1$, benzylamide, 11,15-bis(tetrahydropyran-2-yl)ether, by treating the formula-XXXVII compound (2.4 g.) in 100 ml. of benzene with 4 ml. of DBN at 40°–45° C. for 22 hr. The mixture is cooled, diluted with 25 ml. of benzene, and washed with 25 ml. of ice water. The benzene solution is dried and concentrated. The residue, an oil, is essentially the enol ether, (5Z)-9-deoxy-6,9α-epoxy-Δ$^5$-PGF$_1$, benzylamide, 11,15-bis(-tetrahydropyran-2-yl ether).

The above product is converted to the formula-XXXVIII 6-keto compound by treating with 50 ml. of tetrahydrofuran-5% hydrochloric acid (9:1) at about 25° C. for 15 min. The mixture is diluted with 50 ml. of brine and extracted with ethyl acetate. The organic phase is washed with brine, dried and concentrated to yield the formula-XXXVIII bis-(THP ether), 2.0 g., an oil.

III. Next is prepared the formula-XXXIX 6-keto-PGE$_1$, benzylamide, 11,15-bis(tetrahydropyran-2-yl ether). The above formula-XXXVIII PGF$_1$ compound, (1.0 g.) is oxidized in 25 ml. of acetone with Jones reagent (2 ml.) at −10 to −20° C., adding the reagent dropwise over 2 min. The mixture is stirred for 30 min. and the reaction is quenched with 2 ml. of isopropyl alcohol. The mixture is diluted with brine and extracted with ethyl acetate. The organic phase is washed with brine, dried over sodium sulfate, and concentrated to the formula-XXXIX bis(THP ether), 0.97 g.

IV. Finally, the title compound is obtained by hydrolyzing the product of III above (0.97 g.) in 20 ml. of acetic acid-water-tetrahydrofuran (20:10:3) at 40°–45° C. for 3.5 hr. The solution is diluted with 30 ml. of water and freeze-dried. The residue is chromatographed on Florisil ®, eluting with acetone (0-100%)-methylene chloride to yield the formula-XL title compound, 0.22 g. plus another 0.07 g. from rechromatographing a mixture with less polar material. The product has $R_f$ 0.24 in acetone-methylene chloride (1:1), and NMR peaks at 7.25, 6.5–6.8, 5.4–5.7, 4.2–4.5, 3.5–4.2, 1.9–3.0, and 0.3–1.9δ.

EXAMPLE 14

6-Keto-PGE₁, Anilide (Formula XL)

I. Refer to Chart G. There is first prepared the formula-XXXVII 11,15-bis(tetrahydropyran-2-yl ether). Following the procedure of Example 11-I, the 5ξ-iodo-9-deoxy-6ξ,9α-epoxy-PGF₁, anilide (Preparation 12, 1.8 g.) is reacted with dihydropyran. The product, 3.5 g., is chromatographed on silica gel, eluting with acetone (5–20%)-methylene chloride to yield the bis(THP ether), 2.3 g. having $R_f$ 0.29 (TLC on silica gel in acetone (10%)-methylene chloride).

II. There is next prepared the formula-XXXVIII 6-keto-PGF₁α, anilide, 11,15-bis(tetrahydropyran-2-yl ether) using the above formula-XXXVII compound and following the procedure of Example 11-II. The product, 1.98 g., is chromatographed on silica gel, eluting with acetone (10–70%)-methylene chloride to yield the product, 0.53 g., having $R_f$ 0.66 (TLC on silica gel in acetone-methylene chloride (1:1)).

III. Next is prepared the formula-XXXIX 6-keto-PGE₁, anilide, 11,15-bis(tetrahydropyran-2-yl ether) using the above formula-XXXVIII compound and following the procedure of Example 11-III, to obtain 0.54 g. of oil.

IV. Finally, the title compound is obtained by hydrolyzing the product of III above following the procedure of Example 11-IV. The product is chromatographed on silica gel, eluting with acetone (10–60%)-methylene chloride to obtain the title compound, 0.18 g., having $R_f$ 0.33 (TLC on silica gel in acetone-methylene chloride (1:1)), high resolution mass spectral peak (TMS derivative) at 659.3837, and infrared absorption peaks at 3460, 3400, 3300, 1750, 1725, 1705, 1660, 1600, 1500, 1310, 1290, 1260, 1155, 1100, 1065, 1030, 970, 755, and 690 cm⁻¹.

EXAMPLE 15

6-Keto-PGE₁, p-Phenylphenacyl Ester (Formula VI).

Refer to Chart B. Following the procedures of Example 11, the formula-VII product of Preparation 4, 5ξ-iodo-9-deoxy-6,9-epoxy-PGF₁α, p-phenylphenacyl ester, is converted, first to its bis(THP ether), then to the formula-IV 6-keto-PGF₁α-type compound which is oxidized at the C-9 position to the formula-V compound which is finally hydrolyzed to the formula-VI title compound.

Following the procedures of Example 15 and Chart B but replacing the starting material with the corresponding p-phenylphenacyl ester made by methods described herein or known in the art, there are obtained the following formula-VI compunds:
(15S)-15-Methyl-6-keto-PGE₁, p-phenylphenacyl ester
16,16-Dimethyl-6-keto-PGE₁, p-phenylphenacyl ester.

EXAMPLE 16

6-Keto-PGE₁, p-(p-Actamidobenzamido)phenyl Ester (Formula VI)

Refer to Chart B. A solution of the formula-VII 5ξ-iodo-9-deoxy-6,9-epoxy-PGF₁α free acid (Preparation 3) is converted to the mixed anhydride with isobutylchloroformate in the presence of triethylamine in acetone solution at about −10° C. Thereafter the substituted phenyl ester is obtained using p-(p-acetamidobenzamido)phenol in pyridine at about 25° C.

Thereafter following the procedures of Example 11, the bis(THP ether) is formed and converted to the formula-IV 6-keto-PGF₁α-type compound, which is oxidized at the C-9 position and finally deblocked by mild acid hydrolysis to form the title compound of formula VI.

Following the procedures of Example 16 and Chart B, but replacing that starting material of formula VII with the appropriate 5-halo compound and that phenol with the appropriate substituted phenol, there are prepared the following substituted phenyl esters within the scope of formula-VI:
6-keto-PGE₁, p-benzaldehyde semicarbazone ester
(15S)-15-Methyl-6-keto-PGE₁, p-(p-acetamidobenzamido)phenyl ester
16,16-Dimethyl-6-keto-PGE₁, p-(p-acetamidobenzamido)phenyl ester
(15S)-15-Methyl-6-keto-PGE₁, p-benzaldehyde semicarbazone ester
16,16-Dimethyl-6-keto-PGE₁, p-benzaldehyde semicarbazone ester.

I claim:

1. A compound of the formula

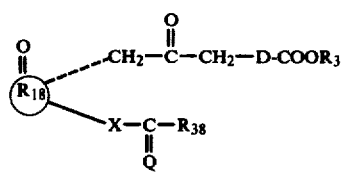

or a mixture comprising that compound and the enantiometer thereof
wherein D is
(1) —(CH₂)₃—C(R₂)₂—
(2) —CH₂—O—CH₂—Y— or
(3) —CH₂CH=CH—
wherein d is zero to 5, R₂ is hydrogen, methyl, or fluoro, being the same or different with the proviso that one R₂ is not methyl when the other is fluoro, and Y is a valence bond, —CH₂— or —(CH₂)₂—,
wherein Q is

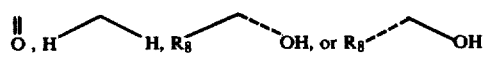

wherein R₈ is hydrogen, methyl, or ethyl, wherein R₃ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

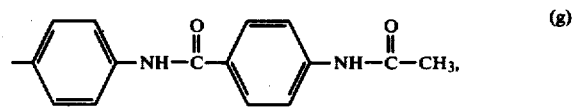

-continued (h) [structure: phenyl-NH-C(=O)-phenyl]

(i) [structure: phenyl-NH-C(=O)-CH₃]

(j) [structure: phenyl-NH-C(=O)-NH₂]

(k) [structure: phenyl-CH=N-NH-C(=O)-NH₂]

(l) [structure: 2-naphthyl]

$$-\overset{|}{\underset{R_{11}}{CH}}-\overset{O}{\overset{\|}{C}}-R_{10}$$

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_{18}$ is

[six cyclopentane ring structures with positions 8, 9, 12 labeled, with substituents OH, OH, (blank), CH₂, (double bond), or CH₂OH]

wherein $R_{38}$ is (1) $-\overset{R_5}{\underset{R_6}{C}}-C_gH_{2g}-CH_3$ or (2) $-CH_2\underset{H}{\overset{}{C}}=\underset{H}{\overset{CH_2CH_3}{C}}$ wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro, and wherein X is
(1) trans—CH=CH—
(2) cis—CH=CH—
(3) —C≡C—
(4) —CH₂CH₂—, including the lower alkanoates thereof.

2. A compound according to claim 1 wherein $R_{18}$ is

[cyclopentane structure with OH]

3. A compound according to claim 2 wherein D is $-(CH_2)_d-C(R_2)_2-$.

4. A compound according to claim 3 wherein D is $-(CH_2)_3-$.

5. A compound according to claim 4 wherein X is trans—CH=CH—.

6. A compound according to claim 5 wherein Q is $$\overset{\|}{O}$$

7. 6,15-Diketo-PGE₁, a compound according to claim 6.

8. A compound according to claim 5 wherein Q is

[structure: R₈ and OH on carbon]

wherein $R_8$ is hydrogen, methyl or ethyl.

9. A compound according to claim 8 wherein $R_8$ is hydrogen.

10. 6-Keto-PGE₁, methyl ester, a compound according to claim 9.

11. 6-Keto-PGE₁, a compound according to claim 9.

12. 6-Keto-PGE₁, sodium salt, a compound according to claim 9.

13. 6-Keto-PGE₁, p-phenylphenacyl ester a compound according to claim 9.

14. 6-Keto-PGE₁, p-(p-acetamidobenzamido)phenyl ester, a compound according to claim 9.

15. 6-Keto-PGE₁, p-benzaldehyde semicarbazone ester, a compound according to claim 9.

16. 16,16-Dimethyl-6-keto-PGE₁, a compound according to claim 9.

17. 16,16-Dimethyl-6-keto-PGE₁, p-phenylphenacyl ester, a compound according to claim 9.

18. 16,16-Dimethyl-6-keto-PGE₁, p-(p-acetamidobenzamido)phenyl ester, a compound according to claim 9.

19. 16,16-Dimethyl-6-keto-PGE₁, p-benzaldehyde semicarbazone ester, a compound according to claim 9.

20. A compound according to claim 8 wherein $R_8$ is methyl.

21. 15(S)-15-Methyl-6-keto-PGE₁, a compound according to claim 20.

22. 15(S)-15-Methyl-6-keto-PGE₁, p-phenylphenacyl ester, a compound according to claim 20.

23. 15(S)-15-Methyl-6-keto-PGE₁, p-(p-acetamidobenzamido)phenyl ester, a compound according to claim 20.

24. 15(S)-15-Methyl-6-keto-PGE₁, benzaldehyde semicarbazone ester, a compound according to claim 20.

25. A compound according to claim 5 wherein Q is

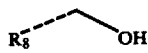

wherein $R_8$ is hydrogen, methyl, or ethyl.

26. (15R)-15-Methyl-6-keto-PGE$_1$, a compound according to claim 25.

27. A compound according to claim 4 wherein X is —C≡C—.

28. A compound according to claim 27 wherein Q is

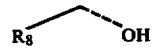

wherein $R_8$ is hydrogen, methyl, or ethyl.

29. 6-Keto-13,14-didehydro-PGE$_1$, a compound according to claim 28.

30. A compound according to claim 27 wherein Q is

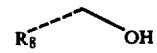

wherein $R_8$ is hydrogen, methyl, or ethyl.

31. 6-Keto-13,14-didehydro-(15R)-PGE$_1$, a compound according to claim 30.

32. A compound according to claim 4 wherein wherein X is —CH$_2$CH$_2$—.

33. 6-Keto-13,14-dihydro-PGE$_1$, a compound according to claim 32.

34. A compound according to claim 3 wherein D is —(CH$_2$)$_2$—CF$_2$—.

35. A compound according to claim 34 wherein X is trans-CH=CH—.

36. A compound according to claim 35 wherein Q is

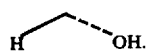

37. 2,2-Difluoro-6-keto-PGE$_1$, methyl ester, a compound according to claim 36.

38. 2,2-Difluoro-16,16-dimethyl-6-keto-PGE$_1$, methyl ester, a compound according to claim 36.

39. A compound according to claim 35 wherein Q is

40. 2,2-Difluoro-(15S)-15-methyl-6-keto-PGE$_1$, methyl ester, a compound according to claim 39.

41. A compound according to claim 34 wherein X is —C≡C—.

42. 2,2-Difluoro-13,14-didehydro-6-keto-PGE$_1$, methyl ester, a compound according to claim 41.

43. A compound according to claim 34 wherein X is —CH$_2$CH$_2$—.

44. 2,2-Difluoro-13,14-dihydro-6-keto-PGE$_1$, methyl ester, a compound according to claim 43.

* * * * *